(12) United States Patent
Patil et al.

(10) Patent No.: US 8,553,219 B2
(45) Date of Patent: Oct. 8, 2013

(54) COMMON DETECTOR FOR COMBINED RAMAN SPECTROSCOPY-OPTICAL COHERENCE TOMOGRAPHY

(75) Inventors: Chetan A. Patil, Nashville, TN (US); Anita Mahadevan-Jansen, Nashville, TN (US); Antonius Gerardus Johannes Maria Van Leeuwen, Bussum (NL); Jeroen Kalkman, Utrecht (NL)

(73) Assignees: Vanderbilt University, Nashville, TN (US); Academisch Medisch Centrum Bu de Universiteit van Amsterdam, Amsterdam (NL)

( * ) Notice: Subject to any disclaimer, the term of this patent is extended or adjusted under 35 U.S.C. 154(b) by 354 days.

(21) Appl. No.: 13/012,529

(22) Filed: Jan. 24, 2011

(65) Prior Publication Data

US 2012/0188538 A1 Jul. 26, 2012

(51) Int. Cl.
*G01J 3/44* (2006.01)
*G01J 3/45* (2006.01)
*G01N 21/00* (2006.01)
*G01B 9/02* (2006.01)

(52) U.S. Cl.
USPC ............................. 356/301; 356/73; 356/456

(58) Field of Classification Search
USPC ............................ 356/456, 301, 73, 326, 479
See application file for complete search history.

(56) References Cited

U.S. PATENT DOCUMENTS 7,075,658 B2 * 7/2006 Izatt et al. ..................... 356/479
8,016,419 B2 * 9/2011 Zhang et al. .................. 351/206
2009/0021724 A1 * 1/2009 Mahadevan-Jansen et al. ................................ 356/73
2010/0245766 A1 * 9/2010 Zhang et al. .................. 351/206
2010/0315632 A1 * 12/2010 Brennan, III ................. 356/301

OTHER PUBLICATIONS

Patil, Chetan A. et al., Structural and biochemical characterization of the rat retina with combined Raman spectroscopy-spectral domain optical coherence tomography (RS-SDOCT), Proc. SPIE 7550, Ophthalmic Technologies XX, vol. 75501 B (Mar. 2, 2010), pp. 1-6.*
Patil, Chetan A. et al., Integrated system for combined Raman spectroscopy-spectral domain optical coherence tomography, Journal of Biomedical Optics, vol. 16(1), No. 011007 (Jan. 2011), pp. 1-10.*
Patil, Chetan A. et al., Combined Raman spectroscopy and optical coherence tomography device for tissue characterization, Optics Letters, vol. 33, No. 10 (May 15, 2008), pp. 1135-1137.*

(Continued)

*Primary Examiner* — Gregory J Toatley
*Assistant Examiner* — Willie Merrell, II
(74) *Attorney, Agent, or Firm* — Tim Tingkang Xia, Esq.; Morris Manning & Martin, LLP

(57) ABSTRACT

An apparatus includes first and second light sources for respectively generating broadband and monochromatic lights, a beamsplitter optically coupled to the first light source for splitting the broadband light into a reference light and a sample light, a reference arm optically coupled to the beamsplitter for receiving the reference light and returning the received reference light into the beamsplitter, a sample arm optically coupled to the beamsplitter and the second light source for combining the sample and monochromatic lights, delivering the combined light to the target of interest, collecting a backscattering light and a Raman scattering light generated from interaction of the combined light with the target of interest, returning the backscattering light into the beamsplitter so as to generate an interference signal between the returned backscattering light and the returned reference light in the beamsplitter, and directing the Raman scattering light in an output optical path.

30 Claims, 9 Drawing Sheets

(56) References Cited

OTHER PUBLICATIONS

J. G. Fujimoto, M. E. Brezinski, G. J. Tearney, S. A. Boppart, B. Bouma, M. R. Hee, J. F. Southern and E. A. Swanson, "Optical biopsy and imaging using optical coherence tomography," Nat Med 1(9), 970-972 (1995).

A. Mahadevan-Jansen, "Raman Spectroscopy: From Benchtop to Bedside," in Biomedical Photonics Handbook T. Vo Dinh, Ed., pp. 30:31-27, CRC Press, Boca Raton, FL (2003).

C. Bowd, L. M. Zangwill, C. C. Berry, E. Z. Blumenthal, C. Vasile, C. Sanchez-Galeana, C. F. Bosworth and P. A. Sample, "Detecting early glaucoma by assessment of retinal nerve fiber layer thickness and visual function," Invest Ophth Vis Sci 42(9), 1993-2003 (2001).

G. Zuccaro, N. Gladkova, J. Vargo, F. Feldchtein, E. Zagaynova, D. Conwell, G. Falk, J. Goldblum, J. Dumot, J. Ponsky, G. Gelikonov, B. Davros, E. Donchenko and J. Richter, "Optical coherence tomography of the esophagus and proximal stomach in health and disease," Am J Gastroenterol 96(9), 2633-2639 (2001).

M. Mogensen, T. M. Joergensen, B. M. Nurnberg, H. A. Morsy, J. B. Thomsen, L. Thrane and G. B. Jemec, "Assessment of optical coherence tomography imaging in the diagnosis of non-melanoma skin cancer and benign lesions versus normal skin: observer-blinded evaluation by dermatologists and pathologists," Dermatol Surg 35(6), 965-972 (2009).

F. J. van der Meer, D. J. Faber, D. M. B. Sassoon, M. C. Aalders, G. Pasterkamp and T. G. van Leeuwen, "Localized measurement of optical attenuation coefficients of atherosclerotic plaque constituents by quantitative optical coherence tomography," Ieee T Med Imaging 24(10), 1369-1376 (2005).

I. Cilesiz, P. Fockens, R. Kerindongo, D. Faber, G. Tytgat, F. ten Kate and T. van Leeuwen, "Comparative optical coherence tomography imaging of human esophagus: How accurate is localization of the muscularis mucosae?," Gastrointest Endosc 56(6), 852-857 (2002).

A. Mahadevan-Jansen, M. F. Mitchell, N. Ramanujam, A. Malpica, S. Thomsen, U. Utzinger and R. Richards-Kortum, "Near-infrared Raman spectroscopy for in vitro detection of cervical precancers," Photochem Photobiol 68(1), 123-132 (1998).

C. A. Lieber, S. K. Majumder, D. L. Ellis, D. D. Billheimer and A. Mahadevan-Jansen, "In vivo nonmelanoma skin cancer diagnosis using Raman microspectroscopy," Laser Surg Med 40(7), 461-467 (2008).

A. S. Haka, K. E. Shafer-Peltier, M. Fitzmaurice, J. Crowe, R. R. Dasari and M. S. Feld, "Diagnosing breast cancer by using Raman spectroscopy," Proc Natl Acad Sci U S A 102(35), 12371-12376 (2005).

M. G. Shim, L. M. Song, N. E. Marcon and B. C. Wilson, "In vivo near-infrared Raman spectroscopy: demonstration of feasibility during clinical gastrointestinal endoscopy," Photochem Photobiol 72(1), 146-150 (2000).

A. C. Ko, L. P. Choo-Smith, M. Hewko, L. Leonardi, M. G. Sowa, C. C. Dong, P. Williams and B. Cleghorn, "Ex vivo detection and characterization of early dental caries by optical coherence tomography and Raman spectroscopy," J Biomed Opt 10(3), 031118 (2005).

C. A. Patil, N. Bosschaart, M. D. Keller, T. G. van Leeuwen and A. Mahadevan-Jansen, "Combined Raman spectroscopy and optical coherence tomography device for tissue characterization," Opt Lett 33(10), 1135-1137 (2008).

J. W. Evans, R. J. Zawadzki, R. Liu, J. W. Chan, S. M. Lane and J. S. Werner, "Optical coherence tomography and Raman spectroscopy of the ex-vivo retina," J Biophotonics 2(6-7), 398-406 (2009).

J. J. Baraga, M. S. Feld and R. P. Rava, "Rapid near-Infrared Raman-Spectroscopy of Human Tissue with a Spectrograph and Ccd Detector," Appl Spectrosc 46(2), 187-190 (1992).

G. Hausler and M. W. Lindner, ""Coherence Radar" and "Spectral Radar"—New Tools for Dermatological Diagnosis," J Biomed Opt 3(1), 21-31 (1998).

N. N. Boustany, M. R. Manoharan, R. R. Dasari and M S. Feld, "Ultraviolet resonance Raman spectroscopy of bulk and microscopic human colon tissue," Appl Spectrosc 54(1), 24-30 (2000).

T. Kawabata, T. Mizuno, S. Okazaki, M. Hiramatsu, T. Setoguchil, H. Kikuchi, M. Yamamoto, Y. Hiramatsu, K. Kondo, M. Baba, M. M Ohta, K. K Kamiya, T. Tanaka, S. Suzuki and H. Konno, "Optical diagnosis of gastric cancer using near-infrared multichannel Raman spectroscopy with a 1064-nm excitation wavelength," J Gastroenterol 43(4), 283-290 (2008).

R. Leitgeb, C. K. Hitzenberger and A. F. Fercher, "Performance of fourier domain vs. time domain optical coherence tomography," Opt Express 11(8), 889-894 (2003).

M. Wojtkowski, R. Leitgeb, A. Kowalczyk, T. Bajraszewski and A. F. Fercher, "In vivo human retinal imaging by Fourier domain optical coherence tomography," J Biomed Opt 7(3), 457-463 (2002).

C. A. Lieber and A. Mahadevan-Jansen, "Automated method for subtraction of fluorescence from biological Raman spectra," Appl Spectrosc 57(11), 1363-1367 (2003).

M. D. Carden and M. D. Morris, "Application of vibrational spectroscopy to the study of mineralized tissues (review)," J . Biomed Opt 5(3), 259-268 (2000).

A. Ascenzi and C. Fabry, "Technique for dissection and measurement of refractive index of osteones," J Biophys Biochem Cytol 6(1), 139-142 (1959).

J. R. Beattie, S. Brockbank, J. J. McGarvey and W. J. Curry, "Effect of excitation wavelength on the Raman spectroscopy of the porcine photoreceptor layer from the area centralis," Mol Vis 11(825-832 (2005).

J. R. Beattie, S. Brockbank, J. J. McGarvey and W. J. Curry, "Raman microscopy of porcine inner retinal layers from the area centralis," Mol Vis 13(1106-1113 (2007).

H. F. Ding, J. Q. Lu, W. A. Wooden, P. J. Kragel and X. H. Hu, "Refractive indices of human skin tissues at eight wavelengths and estimated dispersion relations between 300 and 1600 nm," Phys Med Biol 51(6), 1479-1489 (2006).

H. G. M. Edwards, D. E. Hunt and M. G. Sibley, "FT-Raman spectroscopic study of keratotic materials: horn, hoof and tortoiseshell," Spectrochimica Acta Part A: Molecular and Biomolecular Spectroscopy 54(5), 745-757 (1998).

T. R. Arnett and B. Henderson, Methods in Bone Biology, Chapman and Hall, New York (1998).

M. Ruggeri, G. Tsechpenakis, S. Jiao, M. E. Jockovich, C. Cebulla, E. Hernandez, T. G. Murray and C. A. Puliafito, "Retinal tumor imaging and volume quantification in mouse model using spectral-domain optical coherence tomography," Opt Express 17(5), 4074-4083 (2009).

K. H. Kim, M. Puoris'haag, G. N. Maguluri, Y. Umino, K. Cusato, R. B. Barlow and J. F. de Boer, "Monitoring mouse retinal degeneration with high-resolution spectral-domain optical coherence tomography," J Vis 8(1), 17 11-11 (2008).

J. V. Glenn, J. R. Beattie, L. Barrett, N. Frizzell, S. R. Thorpe, M. E. Boulton, J. J. McGarvey and A. W. Stitt, "Confocal Raman microscopy can quantify advanced glycation end product (AGE) modifications in Bruch's membrane leading to accurate, nondestructive prediction of ocular aging," Faseb J 21(13), 3542-3552 (2007).

J. Lademann, N. Otberg, H. Richter, L. Meyer, H. Audring, A. Teichmann, S. Thomas, A. Kneittel and W. Sterry, "Application of optical non-invasive methods in skin physiology: a comparison of laser scanning microscopy and optical coherent tomography with histological analysis," Skin Research and Technology 13(2), 119-132 (2007).

P. J. Caspers, G. W. Lucassen, R. Wolthuis, H. A. Bruining and G. J. Puppels, "In vitro and in vivo Raman spectroscopy of human skin," Biospectroscopy 4(5 Suppl), S31-39 (1998).

S. H. Yun, G. Tearney, J. de Boer and B. Bouma, "Motion artifacts in optical coherence tomography with frequency-domain ranging," Opt Express 12(13), 2977-2998 (2004).

C. Dorrer, N. Belabas, J. P. Likforman and M. Joffre, "Spectral resolution and sampling issues in Fourier-transform spectral interferometry," J. Opt. Soc. Am. B-Opt. Phys. 17(10), 1795-1802 (2000).

C. L. Evans, E. O. Potma, M. Puoris'haag, D. Cote, C. P. Lin and X. S. Xie, "Chemical imaging of tissue in vivo with video-rate coherent anti-Stokes Raman scattering microscopy," P Natl Acad Sci USA 102(46), 16807-16812 (2005).

(56) References Cited

OTHER PUBLICATIONS

D. L. Marks and S. A. Boppart, "Nonlinear interferometric vibrational imaging," Phys Rev Lett 92(12),—(2004).

Penn, J. S., Tolman, B. L. and Lowery, L. A., "Variable oxygen exposure causes preretinal neovascularization in the newborn rat," Invest Ophthalmol Vis Sci 34(3), 576-585 (1993).

Roberto, K. A., Tolman, B. L. And Penn, J. S., "Long-term retinal vascular abnormalities in an animal model of retinopathy of prematurity," Curr Eye Res 15(9), 932-937 (1996).

Mahadevan-Jansen, A. And Richards-Kortum, R., "Raman Spectrscopy for the Detection of Cancers and Precancers," Journal of Biomedical Optics 1(1), 31-70 (1996).

* cited by examiner

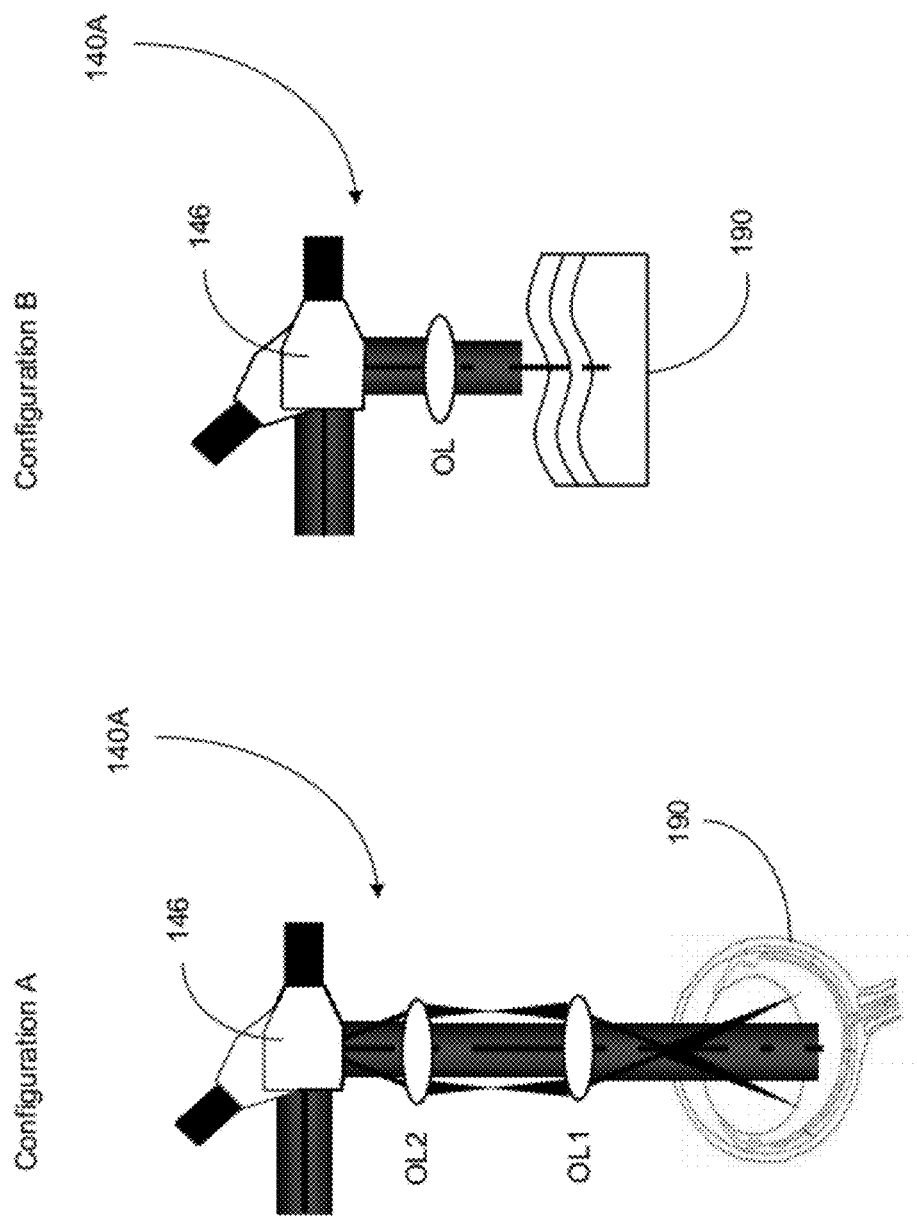

COMMON DETECTOR FOR COMBINED RAMAN SPECTROSCOPY-OPTICAL COHERENCE TOMOGRAPHY

STATEMENT OF FEDERALLY-SPONSORED RESEARCH

This invention is made with government support awarded by the National Institutes of Health of the United States under Contract No. R21 CA133477. The government has certain rights to this invention.

CROSS-REFERENCE TO RELATED PATENT APPLICATION

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference is individually incorporated by reference. In terms of notation, hereinafter, "[n]" represents the nth reference cited in the reference list. For example, [13] represents the 13th reference cited in the reference list, namely, C. A. Patil, N. Bosschaart, M. D. Keller, T. G. van Leeuwen and A. Mahadevan-Jansen, "Combined Raman spectroscopy and optical coherence tomography device for tissue characterization," Opt Lett 33(10), 1135-1137 (2008).

FIELD OF THE INVENTION

The present invention relates generally to a system for biochemical and structural characterization of a target of interest of a living subject, and more particularly to a system that integrates Raman spectroscopy (RS) and optical coherence tomography (OCT) with a common detection arm for both the RS and OCT, for non-invasive evaluation of the biochemical compositions and morphological details of a target of interest of a living subject and applications of the same.

BACKGROUND OF THE INVENTION

Both optical imaging and spectroscopy have been applied to the non-invasive characterization of tissues. Imaging techniques, such as optical coherence tomography (OCT) [1], excel at relaying images of tissue microstructure while spectroscopic methods, such as Raman spectroscopy (RS) [2], are capable of probing the molecular composition of tissue with excellent specificity. The ability of the OCT to perform real-time cross-sectional imaging with micrometer-scale resolution has been utilized for both quantitative and qualitative assessment of tissues in a wide range of applications. For example, quantitative measurements of retinal nerve fiber layer thickness can provide valuable information for glaucoma assessment [3], while qualitative analysis of the esophageal epithelium can identify characteristic features of Barrett's dysplasia [4]. Although visualization of tissue microstructures is often sufficient to characterize tissue type, different structural features can often have a fairly similar appearance in the OCT despite having different underlying molecular makeups [5-7]. This limitation results from the fact that the OCT images are simply maps of reflectivity and do not directly reveal the molecular composition of the sample. The RS, on the other hand, can generate in-elastic scattering spectra with sharp spectral features corresponding to the vibrational modes of biological molecules intrinsic to the sample. The RS has demonstrated the ability to characterize the molecular features of pathology in a number of tissues, including the cervix [8], skin [9], breast [10], and GI tract [11]. In contrast to the OCT, the primary limitation of the RS is that the weak nature of in-elastic scattering precludes rapid spectral imaging over a large spatial area. Clearly, characterization of both the morphological and biochemical composition could compensate for the limitations of both the RS and OCT and allow for a more complete analysis of tissues. For example, the detection of early dental caries has already been identified as a potential application where the mutual benefit of morphological and biochemical characterization OCT and RS can be beneficial [12]. The mutually complementary strengths and limitations of the RS and OCT are well suited for integration into a single instrument for more thorough tissue analysis. The realization of such an instrument allows data collected from the two modalities to augment one another and could advance the biomedical applications of the RS and OCT beyond what is possible with either technique independently.

The most straightforward approach for combination of the RS and OCT into a single instrument includes integrating the sampling optics while maintaining independent detection hardware. To date, the two reports of instruments combining the RS and OCT have pursued the common sample arm approach. The first system combined a time-domain OCT engine using a 1310 nm source and rapid-scanning optical delay reference arm with a 785 nm RS system [13]. This instrument demonstrated the ability of the RS-OCT to perform in vivo analysis and evaluated highly scattering tissues such as the breast and skin. Specifically, the instrument demonstrated the benefits of the RS-OCT by utilizing the OCT to guide Raman spectral acquisition of small (<500 µm) regions of irregular tissue, and utilizing the RS to characterize the biochemical composition of ambiguous structures within an OCT image. A second RS-OCT system combined a Fourier-domain OCT system with an 855 nm broadband source and a spectrometer based detection system (i.e., spectral-domain OCT) with a 633 nm RS system [14]. The advantage of previously reported RS-OCT systems is that the use of independent detection arms allows hardware configurations for each technique to be optimized independently. The drawback, however, is that such configurations require extensive instrumentation that may not be necessary if it are possible to further integrate the two modalities. Since both the RS and OCT can be performed with systems that incorporate a spectrograph and CCD for detection [15, 16], it is possible that a streamlined instrument with a common detection arm can be realized with the appropriate design considerations. The primary challenges in the design of a common-detector RS-OCT system are selection of the appropriate light sources, spectrograph design and selection of appropriate detector architecture.

Therefore, a heretofore unaddressed need exists in the art to address the aforementioned deficiencies and inadequacies.

SUMMARY OF THE INVENTION

One of the objectives of the invention is to provide a combined RS and OCT system with a single detector arm for both the RS and OCT, which allows the use of a single spectrometer to detect both modalities. The advantage of a common detector arm is that it significantly reduces the instrumentational complexity, cost, and size from previously reported RS-OCT systems.

In one aspect, the present invention relates to an apparatus of combining RS and OCT for non-invasively evaluating a target of interest of a living subject. In one embodiment, the apparatus includes a first light source for generating a broadband light characterized with a center wavelength and a spectral bandwidth, and a second light source for generating a monochromatic light at a single wavelength, wherein the first and second light sources are adapted such that resultant Raman scattering spectra and OCT bandwidth have a spectral overlap with each other.

The apparatus also includes a beamsplitter optically coupled to the first light source for receiving the broadband light and splitting the received broadband light into a reference light and a sample light, a reference arm optically coupled to the beamsplitter for receiving the reference light and returning the received reference light into the beamsplitter, and a sample arm optically coupled to the beamsplitter and the second light source for combining the sample light and the monochromatic light, delivering the combined sample and monochromatic light to the target of interest, collecting a backscattering light and a Raman scattering light that are generated from interaction of the sample light and the monochromatic light with the target of interest, respectively, returning the backscattering light into the beamsplitter so as to generate an interference signal between the returned backscattering light and the returned reference light in the beamsplitter, and directing the Raman scattering light in an output optical path. In one embodiment, the beamsplitter comprises an OCT 2×2 fiber coupler.

Further, the apparatus includes a single detector optically coupled to the beamsplitter for collecting the interference signal to provide an interference pattern of the returned backscattering light and the returned reference light, and to the sample arm for collecting the Raman scattering light from the output optical path to provide a Raman scattering spectrum, respectively.

The interference pattern contains information of morphological details of the target of interest, and wherein the Raman scattering spectrum contains information of biochemical contents of the target of interest. In one embodiment, the interference pattern of the interference signal is associated with an OCT image, and wherein a spectral profile of the Raman scattering spectrum includes a plurality of intensity peaks at a plurality of wavelengths, each intensity peak associating with a specific biochemical content of the target of interest.

In one embodiment, the apparatus further comprises a controller in communication with the detector and programmed to correlate the OCT image with the Raman scattering spectrum and determine the structures and biochemical content of the target of interest from the correlated OCT image and Raman scattering spectrum. The controller is a computer having a display for displaying the OCT image and the Raman scattering spectrum.

In one embodiment, the sample arm comprises a collimating lens (CL) optically coupled to the beamsplitter for receiving the sample light and collimating the received sample light into a first optical path, a mirror (M) positioned for reflecting the collimated sample light from the first optical path to a second optical path, a translatable mirror (TM) placed at the second optical path for transmitting the reflected sample light along the second optical path, a dichroic mirror (DM) placed at the second optical path for transmitting the sample light received from the translatable mirror (TM) along the second optical path and reflecting the monochromatic light received from a third optical path into the second optical path, respectively, such that the transmitted sample light and the reflected monochromatic light are combined in the second optical path, a scanning member placed at the second optical path for directing the combined sample and monochromatic light received from the dichroic mirror (DM) to a target of interest along a fourth optical path, and an objective lens (OL) placed at the fourth optical path for focusing the directed sample and monochromatic light received from the scanning member onto the target of interest.

In response, the target of interest backscatters the sample light and the monochromatic light in the forms of a backscattering light and a Raman scattering light, respectively, which are collected and focused to the scanning member by the objective lens (OL), directed by the scanning member along the second optical path to the dichroic mirror (DM), and transmitted by the dichroic mirror (DM) along the second optical path to the translatable mirror (TM), from which the Raman scattering light is reflected to a long pass (LP) filter along the output optical path, while the backscattering light is transmitted along the second optical path to the mirror (M) and reflected thereby along the first optical path to the collimating lens (CL).

The sample arm may also have a dual-band pass filter (BP) and a spatial filter (SF) placed at the third optical path between the dichroic mirror (DM) and the second light source, wherein the dual-band pass filter (BP) is characterized with a central bandpass wavelength corresponding to a wavelength of the monochromatic light.

Additionally, the sample arm further comprises a coupling lens (C) placed at the output optical path for coupling the Raman scattering light transmitted from the long pass (LP) filter to a multimode fiber that is optically connected to the detector.

The scanning member includes at least one of micro-electronic mirrors (MEMS), micro-optoelectrical mirrors (MOEMS), galvanometer devices, rotation motors, translational motors, and a combination of them.

In one embodiment, the apparatus further includes a MEMS optical switch (MOS) optically coupled between the beamsplitter and the detector.

In one embodiment, the MEMS optical switch (MOS), the translatable mirror (TM) and the scanning member are configured such that during an OCT mode, the scanning member scans the combined sample and monochromatic light across the target of interest, the MEMS optical switch (MOS) directs the interference signal received from the beamsplitter to the detector, while the translatable mirror (TM) is positioned such that the Raman scattering light is not collected. During a Raman mode, the scanning member is fixed, the MEMS optical switch (MOS) directs the light received from the beamsplitter away from the detector, while the translatable mirror (TM) reflects the Raman scattering light into the fifth optical path that is coupled to the detector.

The apparatus may also include a multi-function DAQ device for controlling the MEMS optical switch (MOS), the translatable mirror (TM), and the scanning member.

In one embodiment, the reference arm is arranged such that the length of an optical path of the reference light propagating from the beamsplitter through the reference arm and back the beamsplitter is adjustable. The sample light transmits from the beamsplitter through the sample arm to the target of interest, and is backscattered by the target of interest into the beamsplitter through the sample arm along a sample path having a length that is adjustable depending upon the structure of the target of interest to be examined.

In one embodiment, the apparatus may further have three polarization control (PC) paddles optically coupled between the first light source and the beamsplitter, between the beamsplitter and the reference arm, and between the beamsplitter and the sample arm, respectively.

In one embodiment, the first light source comprises light emitting diodes (LEDs), femtosecond lasers or broadband optical amplifiers, and wherein the second light source comprises a laser, wherein the center wavelength is about 855 nm, and wherein the spectral bandwidth is about 40 nm, and wherein the single wavelength is about 785 nm.

In one embodiment, the detector comprises back-illuminated, deep-depletion CCD arrays with cooling mechanisms and a spectrograph that is configured to cover a wavelength range of about 780-920 nm.

In another aspect, the present invention relates to an apparatus for non-invasively evaluating a target of interest of a living subject. In one embodiment, the apparatus includes an OCT system, an RS system, and a single detector for sequentially detecting the OCT images and the Raman spectra.

The OCT system has a broadband light source for emitting a broadband light, a beamsplitter for splitting the broadband light into a reference light and a sample light, a reference arm optically coupled to the beamsplitter for receiving the reference light and returning the received reference light into the beamsplitter, and a sample arm optically coupled to the beamsplitter for receiving the sample light and delivering the received sample light to the target of interest, collecting a backscattering light generated from interaction of the sample light with the target of interest, returning the backscattering light into the beamsplitter so as to generate an interference signal between the returned backscattering light and the returned reference light in the beamsplitter.

In one embodiment, the reference arm is arranged such that the length of an optical path of the reference light propagating from the beamsplitter through the reference arm and back the beamsplitter is adjustable. The sample light transmits from the beamsplitter through the sample arm to the target of interest, and is backscattered by the target of interest into the beamsplitter through the sample arm along a sample path having a length that is adjustable depending upon the structure of the target of interest to be examined.

The RS system has a monochromatic light source optically coupled to the sample arm for emitting a monochromatic light, wherein the monochromatic light is co-aligned with the sample light and delivered to the target of interest by the sample arm, wherein a Raman scattering light is generated from the target of interest interacting with the monochromatic light, and the Raman scattering light is collected and directed by the sample arm to an output optical path In one embodiment, the broadband and monochromatic light sources are adapted such that resultant Raman scattering spectra and OCT bandwidth have a spectral overlap with each other. In one embodiment, the broadband light is characterized with a center wavelength about 855 nm, and a spectral bandwidth about 40 nm, and wherein the monochromatic light has a single wavelength about 785 nm.

The single detector is optically coupled to the beamsplitter for collecting the interference signal to provide an interference pattern of the returned backscattering light and the returned reference light, and to the sample arm for collecting the Raman scattering light from the output optical path to provide a Raman scattering spectrum, respectively.

The interference pattern contains information of morphological details of the target of interest, and wherein the Raman scattering spectrum contains information of biochemical contents of the target of interest. In one embodiment, the interference pattern of the interference signal is associated with an optical coherence tomographic (OCT) image, and wherein a spectral profile of the Raman scattering spectrum includes a plurality of intensity peaks at a plurality of wavelengths, each intensity peak associating with a specific biochemical content of the target of interest.

In one embodiment, the detector comprises back-illuminated, deep-depletion CCD arrays with cooling mechanisms and a spectrograph that is configured to cover a wavelength range of about 780-920 nm.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

FIGS. 2(a) and 2(b) show configurations of sampling optics used for collection from retina, and from standard samples, respectively.

DETAILED DESCRIPTION OF THE INVENTION

Figure 1:
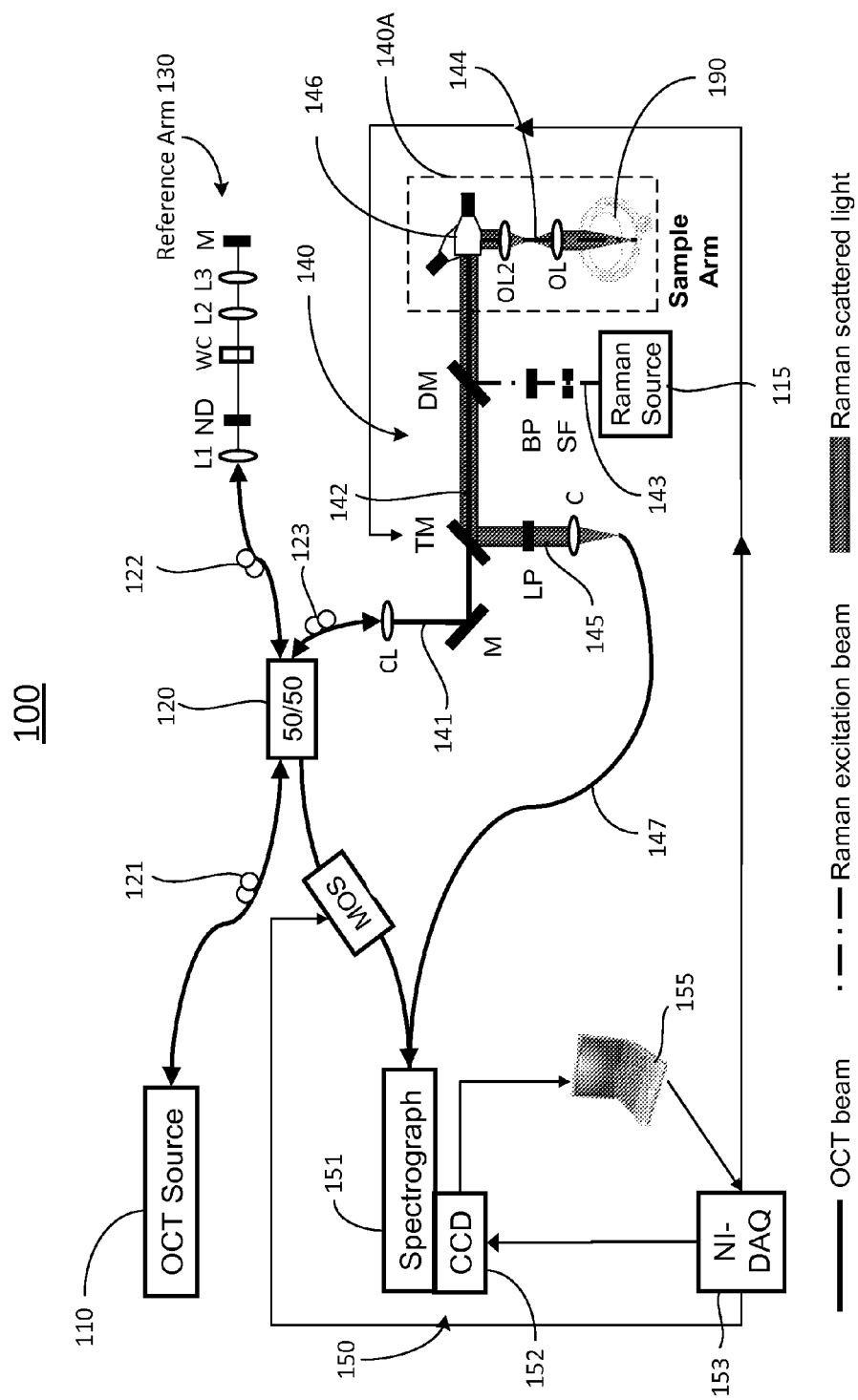
FIG. 1 shows schematically a combined RS-OCT system according to one embodiment of the present invention, PC: Polarization Control paddles, ND: Neutral Density filter, WC: Water filled Cuvette, TM: Translatable Mirror, LP: Long Pass filter, DM: Dichroic Mirror, BP: Band Pass filter, SF: Spatial Filter, XY: XY galvanometer pair, MOS: MEMS Optical Switch, NI-DAQ: National Instruments Multifunction DAQ.

The present disclosure is more particularly described in the following examples that are intended as illustrative only since numerous modifications and variations therein will be apparent to those skilled in the art. Various embodiments of the disclosure are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. The use of examples anywhere in this specification, including examples of any terms discussed herein, is illustrative only, and in no way limits the scope and meaning of the disclosure or of any exemplified term. Likewise, the disclosure is not limited to various embodiments given in this specification.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

As used herein, the terms "comprising," "including," "having," "containing," "involving," and the like are to be understood to be open-ended, i.e., to mean including but not limited to.

As used herein, the term "living subject" refers to a human being such as a patient, or an animal such as a lab testing monkey.

As used herein, the term "Raman spectroscopy" refers to an optical technique that probes the specific molecular content of a sample by collecting in-elastically scattered light. As photons propagate through a medium, they undergo both absorptive and scattering events. In absorption, the energy of the photons is completely transferred to the material, allowing either heat transfer (internal conversion) or re-emission phenomena such as fluorescence and phosphorescence to occur. Scattering, however, is normally an in-elastic process, in which the incident photons retain their energy. In Raman scattering, the photons either donate or acquire energy from the medium, on a molecular level. In contrast to fluorescence, where the energy transfers are on the order of the electronic bandgaps, the energy transfers associated with Raman scattering are on the order of the vibrational modes of the molecule. These vibrational modes are molecularly specific, giving every molecule a unique Raman spectral signature.

Raman scattering is a very weak phenomena, and therefore practical measurement of Raman spectra of a medium requires high power excitation laser sources and extremely sensitive detection hardware. Even with these components, the Raman spectra from tissue are masked by the relatively intense tissue auto-fluorescence. After detection, post processing techniques are required to subtract the fluorescent background and enable accurate visualization of the Raman spectra. Raman spectra are plotted as a function of frequency shift in units of wavenumber ($cm^{-1}$). The region of the Raman spectra where most biological molecules have Raman peaks is from 500 to 2000 $cm^{-1}$. In contrast to fluorescence spectra, Raman spectra have sharp spectral features that enable easier identification of the constituent sources of spectral peaks in a complex sample. In the context of detecting the changes that cancerous tissues undergo, differences in the Raman spectral features that correlate to the increased nucleic acid content in neoplastic cells has observed.

The term "optical coherence tomography" or its acronym "OCT" refers to an interferometric, non-invasive optical tomographic imaging technique offering millimeter penetration (approximately 2-3 mm in tissue) with micrometer-scale axial and lateral resolution. In principle, the OCT is analogous to an optical version of ultrasound. While ultrasound images are formed by a transducer emitting ultrasonic pulses and then time gating detection of the tissue echoes, OCT images are formed by using an interferometer to correlate continuous wave light reflected from a reference mirror at a known distance with light reflected from a highly scattering tissue sample at an equivalent distance. Both techniques essentially time gate a signal backscattered from the tissue, only OCT utilizes low-coherence interferometry rather than pulse-echo delay measurements due to the extremely high speed of light.

A low-coherence Michelson interferometer forms the backbone of an OCT system that includes a broadband laser source illuminating a 50/50 beamsplitter. The two arms of the interferometer in OCT are referred to as the reference and sample arms. In the reference arm, a moving mirror serves to reflect light back towards the beamsplitter for the purpose of correlation with the light backscattered from a biological specimen in the sample arm.

The backscattered light from the reference and sample arms interferes at the beamsplitter and is detector by a photodiode. The amplitude of the detected signal is essentially the reflectivity of the sample as a function of the reference mirror position, which is directly related to depth within the sample, while the axial point-spread function (PSF) is the autocorrelation of the reference electric field, which is equivalent to the Fourier transform of the broadband laser source spectrum. Because the point-spread function and laser spectrum are Fourier pairs, the broader the bandwidth of the laser, the better the axial resolution of the imaging system. Two-dimensional OCT images are built up by transverse scanning the sample beam across the sample and false-color coding the amplitude of the backscattered interference.

The term "point spread function" or its acronym "PSF" refers to the response of an imaging system to a point source or point object. The PSF in many contexts can be thought of as the extended blob in an image that represents an unresolved object. In functional terms it is the spatial domain version of the modulation transfer function. The degree of spreading (blurring) of the point object is a measure for the quality of an imaging system. In incoherent imaging systems such as fluorescent microscopes, telescopes or optical microscopes, the image formation process is linear and described by linear system theory. This means that when two objects A and B are imaged simultaneously, the result is equal to the sum of the independently imaged objects. In other words: the imaging of A is unaffected by the imaging of B and vice versa.

Telecentricity is a special property of certain multi-element lens designs in which the chief rays for all points across the object or image are collimated. For example, telecentricity occurs when the chief rays are parallel to the optical axis, in object and/or image space.

The description will be made as to the embodiments of the present invention in conjunction with the accompanying drawings. In accordance with the purposes of this invention, as embodied and broadly described herein, this invention, in one aspect, relates to a combined RS-OCT system with a common detection arm for both the RS and OCT for non-invasive biochemical and structural evaluations of a target of interest of a living subject. The detector is a spectrograph that is capable of sequential detection of the 855 nm OCT signal and the Raman scatter generated by a 785 nm source. The target of interest can be skin tissues, organ tissues, retina, or any parts of a living subject.

The combined RS-OCT system employing common detection hardware is disclosed and applications of the system for morphological and biochemical characterization of ex vivo rodent calvaria and retina, along with in vivo analysis of human skin are demonstrated. The novel design takes advantage of the fact that spectral domain configurations of the OCT utilize a detection platform similar to the RS and integrates the detection arms of both modalities into a single spectrograph and CCD. The result is a fully integrated system that demonstrates for the first time, to the inventors' knowledge, in vivo characterization of both the biochemical composition and microstructure of tissues with a common-detector RS-OCT system.

Referring to FIG. 1, an integrated RS-OCT system/apparatus 100 is shown according to one embodiment of the present invention. The integrated RS-OCT system 100 includes a first light source 110 for generating a broadband light, a second light source 115 for generating a monochromatic light, a beamsplitter 120, a reference arm 130, and a sample arm 140 and a common detector 150.

The beamsplitter 120 is optically coupled to the first light source 110 for receiving the broadband light and splitting the received broadband light into a reference light and a sample light. The reference arm 130 is optically coupled to the beamsplitter 120 for receiving the reference light and returning the received reference light into the beamsplitter 120. The sample arm 140 is optically coupled to the beamsplitter 120 and the second light source 115 for combining the sample light and the monochromatic light, delivering the combined sample and monochromatic light to the target of interest 190, collecting a backscattering light and a Raman scattering light that are generated from interaction of the sample light and the monochromatic light with the target of interest 190, respectively, returning the backscattering light into the beamsplitter 120 so as to generate an interference signal between the returned backscattering light and the returned reference light in the beamsplitter 120, and directing the Raman scattering light in an output optical path.

In the exemplary embodiment shown in FIG. 1, the sample arm 140 includes a collimating lens (CL) optically coupled to the beamsplitter 140 for receiving the sample light and collimating the received sample light into a first optical path 141, a mirror (M) positioned for reflecting the collimated sample light from the first optical path 141 to a second optical path 142, a translatable mirror (TM) placed at the second optical path 142 for transmitting the reflected sample light along the second optical path 142, a dichroic mirror (DM) placed at the second optical path 142 for transmitting the sample light received from the translatable mirror (TM) along the second optical path 142 and reflecting the monochromatic light received from a third optical path 143 into the second optical path 142, respectively, such that the transmitted sample light and the reflected monochromatic light are combined in the second optical path 142, a scanning member 146 placed at the second optical path 142 for directing the combined sample and monochromatic light received from the dichroic mirror (DM) to a target of interest 190 along a fourth optical path 144, and an objective lens (OL) placed at the fourth optical path 144 for focusing the directed sample and monochromatic light received from the scanning member onto the target of interest 190. Depending upon the target of interest to be evaluated, a second objective lens (OL2) may be inserted at the fourth optical path 144 between the scanning member 146 and the objective lens (OL), as shown in FIG. 2(a). FIG. 2(b) shows a configuration of sampling optics used for collection from standard samples. In one embodiment, the translatable mirror (TM) is mounted onto a translation stage. The scanning member 146 includes at least one of micro-electronic mirrors (MEMS), micro-optoelectrical mirrors (MOEMS), galvanometer devices, rotation motors, translational motors, and a combination of them.

In response, the target of interest 190 backscatters the sample light and the monochromatic light in the forms of a backscattering light and a Raman scattering light, respectively, which are collected and focused to the scanning member by the objective lens (OL), directed by the scanning member 146 along the second optical path 142 to the dichroic mirror (DM), and transmitted by the dichroic mirror (DM) along the second optical path 142 to the translatable mirror (TM), from which the Raman scattering light is reflected to a long pass (LP) filter along the output optical path 145, while the backscattering light is transmitted along the second optical path 142 to the mirror (M) and reflected thereby along the first optical path to the collimating lens (CL).

The sample arm 140 also have a dual-band pass filter (BP) and a spatial filter (SF) placed at the third optical path 143 between the dichroic mirror (DM) and the second light source 115. The dual-band pass filter (BP) is characterized with a central bandpass wavelength corresponding to a wavelength of the monochromatic light.

Additionally, the sample arm 140 further comprises a coupling lens (C) placed at the output optical path 145 for coupling the Raman scattering light transmitted from the long pass (LP) filter to a multimode fiber 147 that is optically connected to the detector 150.

The single detector 150 is optically coupled to the beamsplitter 120 for collecting the interference signal to provide an interference pattern of the returned backscattering light and the returned reference light, and to the sample arm 140 for collecting the Raman scattering light from the output optical path to provide a Raman scattering spectrum, respectively.

The interference pattern contains information of morphological details of the target of interest, and wherein the Raman scattering spectrum contains information of biochemical contents of the target of interest. The interference pattern of the interference signal is associated with an optical coherence tomographic (OCT) image, and wherein a spectral profile of the Raman scattering spectrum includes a plurality of intensity peaks at a plurality of wavelengths, each intensity peak associating with a specific biochemical content of the target of interest.

In order to realize the integrated RS-OCT system 100 with a common detector, the initial concern is selecting light sources 110 and 115 that result in spectral overlap of the Raman scatter spectrum and the OCT bandwidth. The RS of tissues has been reported at wavelengths from the ultraviolet [17] to 1064 nm in the infrared [18]. Typically, sources in the near-infrared are preferred because tissue autofluorescence is reduced. However, Raman scattering intensity and detector responsivity also typically decrease with increasing wavelength. A wavelength stabilized external cavity 785 nm diode laser (Sacher Lasertechnik Group, Marburg, Germany) is selected as the Raman source 115 because tissue autofluorescence is minimized without increasing the wavelength so much as to significantly reduce the collected Raman signal intensity. The OCT can also be performed over a range of wavelengths in the near-infrared. However, it is typically performed near wavelengths at 830 or 1310 nm. The additional benefit of the 785 nm RS source is that the resultant "fingerprint" region for organic molecules, which ranges from 500 to 2000 $cm^{-1}$ relative wavenumbers, spans the wavelength band from 815-930 nm (500-2000 $cm^{-1}$) and nicely overlaps a spectral range where OCT sources are readily available. The selected OCT source 110 (Exalos, Inc., Langhorne, Pa.) is centered at 855 nm with a −3 dB bandwidth of 40 nm and a full spectral width ranging from approximately 800-900 nm, and is thus well suited for integration with the 785 nm RS source. It should be noted that although the RS of tissues is also commonly performed with an 830 nm source, the corresponding fingerprint region (866-995 nm) does not overlap well with any readily available broadband light sources suitable for the OCT. In addition, the quantum efficiency of silicon detectors in the 830 nm fingerprint region is inferior to that of the 785 nm fingerprint region, which is beneficial for both modalities.

After selection of the appropriate sources 110 and 115, it is critical that the design of the detection hardware 150 facilitate both the RS and OCT of tissues. Detectors capable of exceptionally high sensitivity coupled with a resistance to etaloning are necessary to acquire Raman spectra from tissues due to the weak nature of Raman scattering and the relatively intense tissue auto-fluorescence background. The detectors are typically back-illuminated, deep-depletion CCD arrays 152 with cooling mechanisms in place to limit the dark noise. Although the detectors used in the OCT clearly also benefit from low noise, they differ in that they are typically front-illuminated CCD arrays with a large dynamic range and high-speed readout rates. Due to the stringent detector requirements of the RS, a back illuminated, deep-depletion, thermo-electrically cooled 1024×256 CCD camera (Newton 920-BRDD, Andor Technology, Belfast, Northern Ireland) typically used for RS is selected. This detector is capable of 2.5 MHz pixel readout rate and 26 µm×26 µm pixels with a full well capacity at about 180,600 e−/pixel. The read-rate and dynamic range of the camera are similar to the specifications of detectors typically employed for OCT while it is also sensitive enough for detection of tissue Raman signals.

Figure 2C:
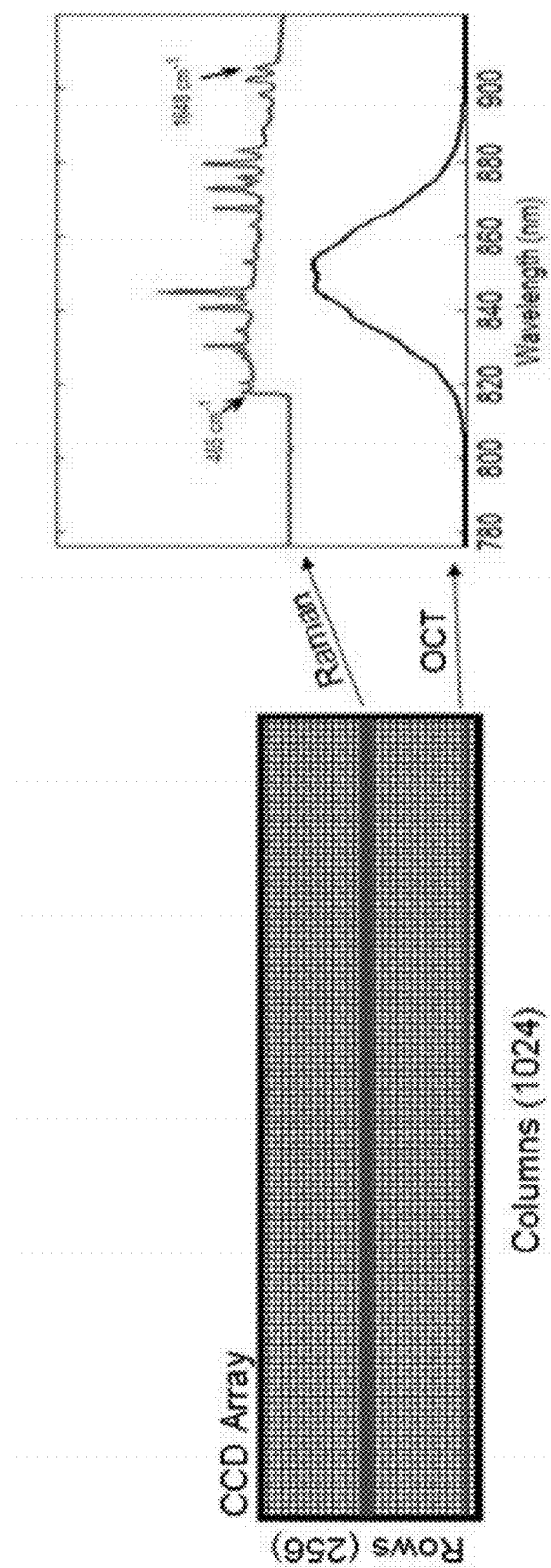
FIG. 2(c) illustrates schematically a CCD array illumination for the RS and OCT, along with the spectral overlap of an example Raman spectrum (acetaminophen) and the OCT source.

The detector is coupled to an f/1.8 imaging spectrograph 151 (magnification=1.13) with a 785 nm Raman holographic transmission grating (Kaiser Optical Systems, Inc., Ann Arbor, Mich.). The spectrograph 151 is configured to cover a wavelength range from 780-920 nm, which spans the full bandwidth of the OCT source and thus does not adversely affect the theoretical axial resolution limit for imaging. The spectral range here corresponds to Raman shifts up to 1870 $cm^{-1}$, which is sufficient to nearly cover the entire range of spectral features arising from tissue. FIG. 2(c) illustrates the detector illumination and the spectral overlap of the Raman fingerprint region and the OCT source spectrum.

In addition to spectral coverage, it is critical that sufficient spectral resolution is achieved for both the RS and OCT. In order to identify the sharp spectral features of tissue Raman signals, a spectral resolution of at least 10 $cm^{-1}$ is necessary. In spectral domain OCT, the maximum depth range is inversely related to the spectral resolution [16]. Therefore, it is important that the spectral resolution is sufficiently high to allow the depth range to exceed the optical penetration depth of the imaging light source, which is generally 1-2 mm in the tissue. The system according to the invention collects light in separate 100 µm multimode (for the RS) and 6 µm single mode (for the OCT) fibers, which are coupled to the spectrograph with a custom input adapter and illuminate different rows of the CCD. The resulting spectral resolution is 0.123 nm for the OCT, and 7 $cm^{-1}$ for the RS. For the OCT, the spectral resolution is back-calculated after the un-aliased axial depth scan range is calibrated by translating a micrometer through the sample arm optical path and determined to be 1.27 mm in air. The spectral resolution ($\delta\lambda$) can be calculated as, $\delta\lambda = \lambda_{center}^2/4 \cdot n \cdot z_{max}$ [16], where $\lambda_{center}$ is the spectrograph center wavelength, n is the index of refraction, and $z_{max}$ is the maximum un-aliased scan range. Calibration of the spectrograph is performed with the atomic emission lines of a Neon-Argon lamp.

As shown in FIG. 1, for such an RS-OCT system 100, the Raman illumination includes free space optics integrated into the OCT sample arm 140. In one embodiment, the multimode shaped source 115 passes through a spatial filter (SF) and a 785 nm bandpass filter (BF) to produce a spectrally and spatially clean, collimated beam. A standard 785 nm Raman dichroic mirror (DM) (Chroma Technologies Co., Bellows Falls, Vt.) allows this beam to be co-aligned with the OCT beam and directed towards the sample 190. During Raman acquisition, the mirrors in the XY galvanometer pair 146 are stationary. Because the galvanometer pair 146 and the objective lens (OL) are arranged in a telecentric manner, the RS can thus be performed along any A-scan in the OCT image. Acquisition from the central A-scan is preferred for maximum Raman signal, but not essential. An achromatic doublet lens (f=30 mm, NA=0.42) serves as the objective and focuses the light to a 15 μm spot. An achromat lens is important to achieve relatively consistent collection efficiency of the Raman scattered light across the entire "fingerprint" region. The axial response of the RS collection is measured by translating a thin (about 12.5 μm) polyethylene sheet through the focus and measuring the intensity of the 1308 cm$^{-1}$ peak. The FWHM of the axial response function is then calculated to be about 425 μm. The power of the Raman beam at the sample is about 40 mW. The Raman scattered light then returns back through the sampling optics and dichroic mirror (DM), and is redirected towards the Raman collection fiber by a mirror mounted to a computer controlled translation stage. Before fiber coupling an 818 nm long pass filter further rejects elastic scatter. In order to characterize the performance of the RS sub-system, spectra are acquired from a silicon wafer ($T_{acq}$=1 sec), and measured the signal-to-noise ratio to about 22.3 dB. During OCT imaging, the translation stage is shifted aside to allow the OCT beam to freely pass. As such, the system 100 does not allow for simultaneous RS and OCT. The two data sets are acquired sequentially. Registration of the Raman collection within the OCT image is performed as described in a previously reported RS-OCT system with independent detection arms [13].

The OCT source 110 is coupled to a 50/50 fiber splitter 120, which directs light to the reference arm 130 and the sample and arms 140. Polarization control paddles 121-123 are placed between the splitter 120 and the OCT source 110, the reference arm 130, and the sample arm 140 to fine tune the splitting ratio and optimize the detected interference signal. The sample arm 140 includes an XY galvanometer pair 146 for generating the transverse scan dimension in the OCT and the achromatic doublet objective lens (OL), which focuses the OCT beam to a spot size of about 18 μm. The objective lens (OL) is selected in order to achieve nearly isotropic spatial resolution, which is important for high quality imaging. The reference arm 130 includes a neutral density (ND) filter, an achromatic objective lens (L1) matching that of the sample, and a mirror (M) for returning the reference light to splitter 120. Insertion of the neutral density filter allows the appropriate level of reference attenuation to optimize imaging sensitivity while preventing saturation of the detector [19]. In one embodiment, the reference arm 130 is arranged such that the length of an optical path of the reference light propagating from the splitter 120 through the reference arm and back to the splitter 120 is adjustable. The optimized sensitivity of the system is measured to be about −86 dB, at which point the corresponding power of the OCT beam at the sample is about 14 μW. The OCT sensitivity can be improved by averaging multiple images, after tomographic reconstruction. When about 25 frames are averaged, the system can achieve a sensitivity of about −100 dB. Care is taken to match the dispersion of the reference arm 130 and the sample arm 140 in order to minimize degradation of the axial resolution. The measured axial resolution is about 11 μm in air (about 8 μm in tissue). An optical MEMS switch (MOS) (Thorlabs, Inc., Newton, N.J.) is placed in the detection arm of the fiber interferometer. During the acquisition of OCT images, the interference signal passes through to the spectrograph, however, during the Raman acquisition, the switch directs the OCT signal returning from the reference arm away from the spectrograph so as not to overwhelm the Raman signal.

In one embodiment, the MEMS optical switch (MOS), the translatable mirror (TM) and the scanning member are configured such that during an OCT mode, the scanning member scans the combined sample and monochromatic light across the target of interest, the MEMS optical switch (MOS) directs the interference signal received from the beamsplitter to the detector, while the translatable mirror (TM) is positioned such that the Raman scattering light is not collected. During a Raman mode, the scanning member is fixed, the MEMS optical switch (MOS) directs the light received from the beamsplitter away from the detector, while the translatable mirror (TM) reflects the Raman scattering light into the fifth optical path that is coupled to the detector.

The entire system 100 is run off a single notebook computer 155 with a LabVIEW software interface. Other types of computers or controllers can be adapted for running the system as well. A multi-function DAQ device 153 (National Instruments Co., Austin, Tex.) allows software control of the optical MEMS switch (MOS), the translation stage mounted mirror (TM), and the XY galvanometer pair 146 in the sample arm 140. As set forth above, the system 100 operates in either the Raman or OCT mode. During the OCT mode, the XY mirrors 146 scan the beam across the sample 190, the MEMS optical switch (MOS) directs the OCT interference signal to the spectrograph 151, and the RS is disabled by positioning the mirror (TM) mounted to the translation stage such that the Raman scatter is not collected. Furthermore, the detector 150 reads out a cropped portion of CCD array that includes only the bottom 20 rows of the chip, as shown in FIG. 2(c). This allows spectra to be collected at the maximum possible line rate of about 2.1 kHz. In the Raman mode, the OCT illumination beam is blocked by the translatable mirror (TM), the XY mirrors 146 are fixed, and the optical MEMS switch (MOS) directs the light from the OCT reference arm away from the spectrograph. The detector 150 then bins the set of rows on the top half of the chip that are illuminated by the Raman signal. During the RS, the last acquired OCT image is retained and the position of the Raman collection is graphically overlaid onto the display to guide the user positioning of the sample 190 and/or XY mirror 146 positioning.

Data processing to produce OCT images and Raman spectra is performed in real-time. The spectrograph calibration, Raman spectra pre-processing and tissue autofluorescence subtraction are performed as described by Lieber et al [21]. To create an OCT image, the reference arm signal is stored before each image acquisition, and then subtracted from subsequent spectra to remove the DC component of the interference signal. After the DC subtraction, the spectrum is inflated and remapped from wavelength space to linear k-space in order to ensure appropriate mapping from the spectral domain to the spatial domain [20]. Fast Fourier transform then produces the depth scan. At this stage, multiple OCT images are averaged to improve imaging sensitivity. After factoring in data transfer and processing time, the display rate of processed OCT images (512×512) is 2 frames/sec. A number of additional system calibrations are necessary prior to processing the Raman spectra. Variations in system throughput are corrected for using a NIST calibrated quartz-tungsten-halogen lamp. In order to account for minor day-to-day variations in the spectral position of the Raman excitation laser line, the relative wavenumber axis is calibrated with standards such as acetaminophen and naphthalene. Laser induced fluorescence from the system optics and general background signal is removed by subtracting a background spectra. After the sample spectrum is white light corrected and background subtracted, the tissue autofluorescence is removed using a modified polynomial fitting algorithm [21].

The utility of a common detector RS-OCT system in the marketplace is broad—any sample whose microstructural architecture and biochemical composition is worth evaluating can benefit from the RS-OCT system. The applications are for biomedical analysis of tissues, both for clinical use on human subjects, and pre-clinical use on animal models. The applications in the skin, breast, retina and murine calvaria have been demonstrated. Other possible target tissues include, but are not limited to, the GI tract, respiratory organs, the vasculature including the coronary arteries, cervix, bladder, etc.

Without intent to limit the scope of the invention, exemplary instruments, apparatus, methods and their related results according to the embodiments of the present invention are given below. The fundamental objective of the following examples is to validate the utility of combined biochemical and structural analysis of biological tissues with the common-detector RS-OCT system. To demonstrate the underlying concept in practice, ex vivo images and spectra are collected from dissected rodent calvaria (skull cap) and the rodent retina. In vivo data of human skin is collected from the palm of a volunteer. All data is collected under protocols approved by the Vanderbilt University institutional review board and institutional animal care and use committee.

Data collection from the rodent retina is performed through the intact eye, and therefore, required a modified instrument (sample arm) configuration, as shown in FIGS. 1 and 2(a), to account for the focusing properties of the eye itself. Because the physical optics of the eye focuses distant light onto the retina, the instrument configuration is modified to illuminate the sample (retina) 190 with collimated light. In the sample optics 140A, a second objective lens (OL2) is inserted to create a 2-f telecentric scan geometry that illuminated the pupil of the eye with a collimated beam ($d_{OCT}$=2.1 mm, $d_{Raman}$=2.4 mm). The additional dispersion introduced in the sample by the second lens and the eye itself is compensated for in the OCT reference arm by adding a matching second objective lens (L2) and a 5 mm water-filled cuvette (WC) in the OCT reference arm. In one embodiment, one or more additional objective lens, such as L3, may be added in the optical path of the OCT reference arm.

Figure 3:
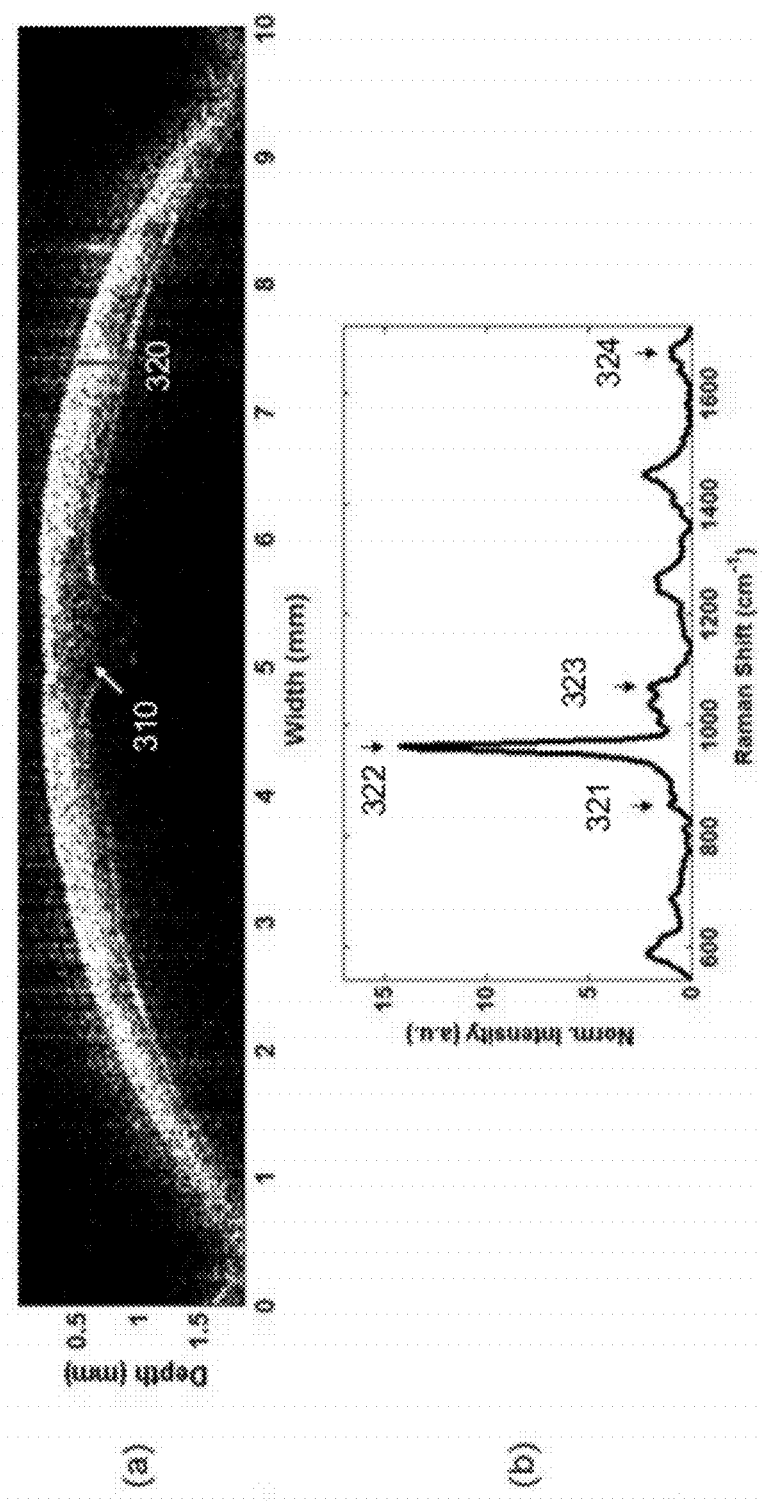
FIG. 3 shows RS-OCT evaluation of a dissected murine calvaria, (a) an OCT image, where arrow 310 indicates dark hypo-reflective region likely associated with the suture of the left and right parietal skull plates, area 320 indicates the region where the corresponding Raman spectrum is acquired, and axial scale assumes $n_{cavana}$=1.55 [23], (b) a Raman spectrum, normalized to mean spectral intensity, where arrows 321-324 indicate positions of peaks typically utilized in Raman spectral analysis of mineralized tissues, including the proline peak at 857 $cm^{-1}$, the phosphate peak at 960 $cm^{-1}$, the carbonate peak at 1072 $cm^{-1}$, the amide I peak at 1667 $cm^{-1}$, respectively.

In order to demonstrate the capability of the common detector RS-OCT system in highly scattering tissues, data shown in FIG. 3 is acquired from the dissected calvaria of a rat/mouse. The OCT image, as shown in FIG. 3(a), is the average of three acquisitions, where arrow 310 indicates dark hypo-reflective region likely associated with the suture of the left and right parietal skull plates. Area 320 indicates the region where the corresponding Raman spectrum is acquired. Axial scale assumes $n_{calvaria}$=1.55 [23]. The image allows clear visualization of the inner and outer surfaces of the calvaria, along with fair contrast between the hyper-reflective mineralized bone tissue and the less reflective collagenous tissue associated with the sutures that hold the plates of the skull together. This is most evident in the center of the image at the suture connecting the left and right parietal plates. The corresponding Raman spectra, as shown in FIG. 3(b) where $t_{acq}$=30 sec, acquired from the sample is representative of a typical Raman signature of the mineralized tissue. Arrows 321-324 indicate positions of features/peaks typically utilized in Raman spectral analysis [22] of mineralized tissues including the subtle proline peak at 857 cm$^{-1}$, the prominent phosphate peak at 960 cm$^{-1}$, the carbonate peak at 1072 cm$^{-1}$, and the amide I peak at 1667 cm$^{-1}$, respectively.

Figure 4:
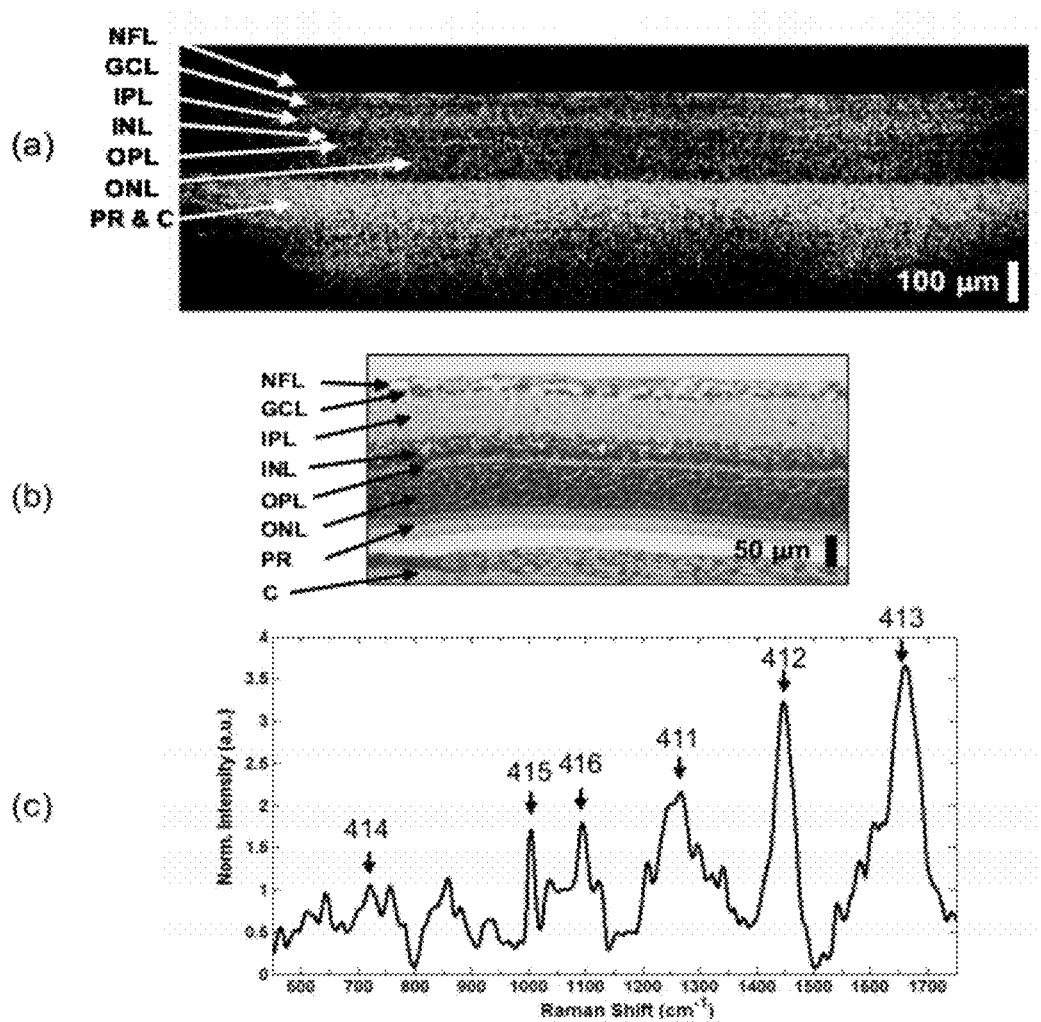
FIG. 4 shows RS-OCT evaluation of the rodent retina, (a) OCT image. The layers of the retina visible, from inner layers to outer layers, include the thin, bright nerve fiber layer (NFL), hypo-reflective ganglion cell layer (GCL), thicker hyper-reflective inner plexiform layer (IPL), the hypo-reflective inner nuclear layer (INL), the thin, bright outer plexiform layer (OPL), the hypo-reflective outer nuclear layer (ONL), and the photoreceptor layer and choroid (PR & C), which are difficult to distinguish and labeled as a single layer. (b) Corresponding histology. (c) Mean Raman spectrum acquired from 5 axes equally spread across the retina. The set of peaks most prominent in the retina are identified, and include amide III (1265 $cm^{-1}$), $CH_x$ (1440 $cm^{-1}$), and amide I (1660 $cm^{-1}$), as well at those from DNA/RNA at 723 $cm^{-1}$, 1003 $cm^{-1}$, 1094 $cm^{-1}$, which are indicated by arrows 411-416, respectively.

As discussed above, the OCT performed in the band from 800-900 nm is best suited for imaging the retina. To demonstrate the ability of the common-detector RS-OCT system to characterize both the morphology and biochemistry of the retina, data shown in FIG. 4 is collected from the retina of a 4 week old rat pup, through the intact eye. The OCT image shown in FIG. 4(a) is an average of 20 OCT frames and is depicted in the false color scale typically associated with the OCT of the retina [24]. The layers of the retina visible, from inner layers to outer layers, include the thin, bright nerve fiber layer (NFL), hypo-reflective ganglion cell layer (GCL), thicker hyper-reflective inner plexiform layer (IPL), the hypo-reflective inner nuclear layer (INL), the thin, bright outer plexiform layer (OPL), the hypo-reflective outer nuclear layer (ONL), and the photoreceptor layer and choroid (PR & C), which are difficult to distinguish and labeled as a single layer. The image demonstrates the sufficient resolution and imaging range of the system to depict the layers of the retina. A set of 5 Raman spectra ($t_{acq}$=90 sec) are acquired from multiple axis across the image to characterize the general Raman signature. In order to achieve sufficient signal-to-noise the Raman power at the sample is increased from 40 mW to 100 mW, which is necessary due to the gradual loss of clarity in the eye after the animal is sacrificed and the lack of pupil dilation. The mean spectrum is acquired from 5 axes equally spread across the retina, and shown in FIG. 4(c). The spectral features show similarities to those reported in the literature [25, 26], including peaks at 1265 cm$^{-1}$ (amide III), 1440 cm$^{-1}$ ($CH_x$), and 1660 cm$^{-1}$ (amide I), indicated respectively by arrows 411-413, which are commonly seen in most soft tissues. Protein signatures present in Raman spectra include those arising from DNA and RNA molecules present in the nuclear layers, the most intense of which occur at 723 cm$^{-1}$, 1003 cm$^{-1}$, 1094 cm$^{-1}$, indicated respectively by arrows 414-416, respectively.

Figure 5:
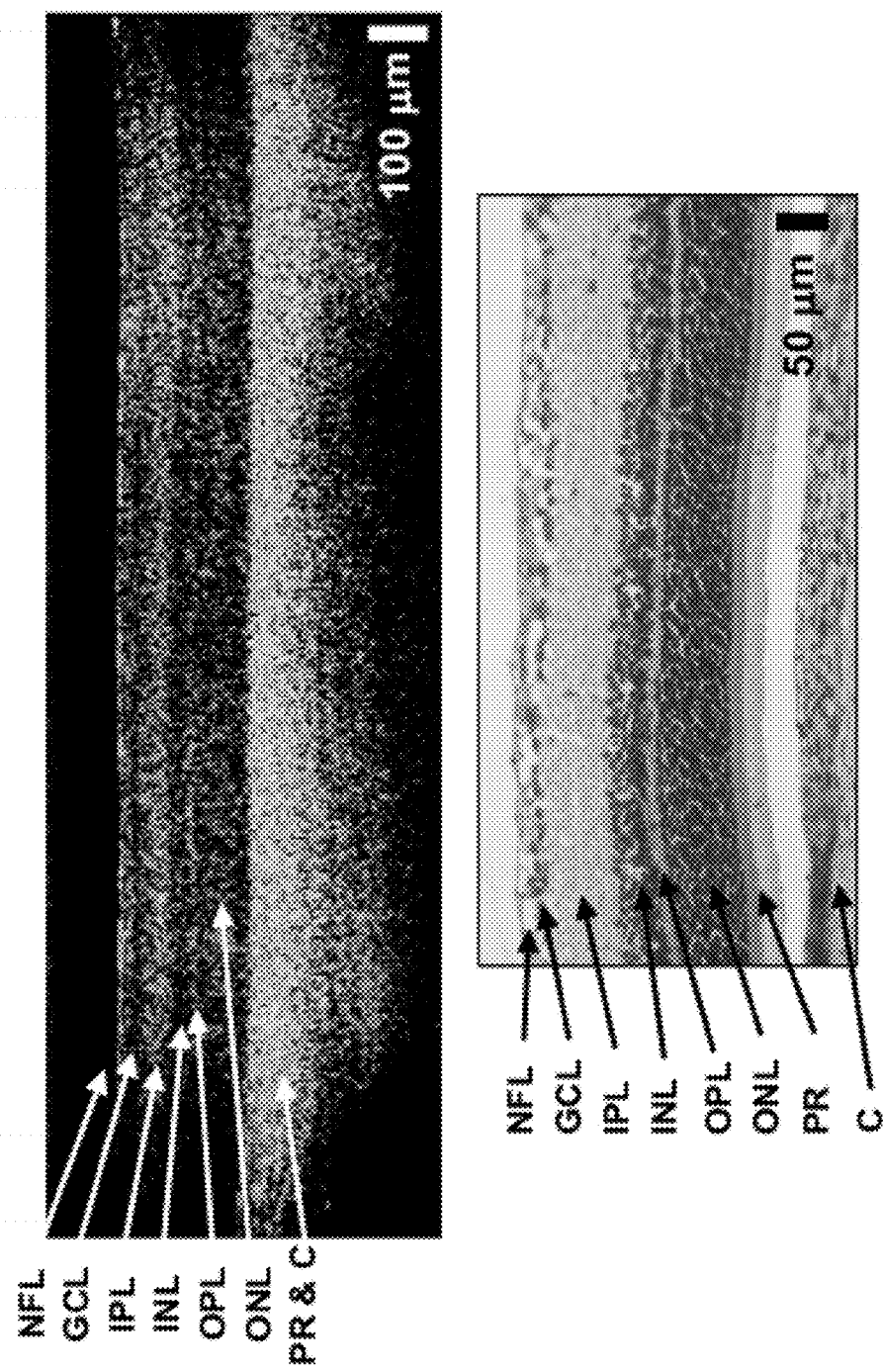
FIG. 5 shows representative OCT and histology of VO 14(12) and. RA P26 eyes. Image depicts the ability of RS-OCT to resolve retinal structure in both the VO and RA rats. The layers of the retina visible, from inner layers to outer layers, include the thin, bright nerve fiber layer (NFL), hypo-reflective ganglion cell layer (GCL), thicker hyper-reflective inner plexiform layer (IPL), the hypo-reflective inner nuclear layer (INL), the thin, bright outer plexiform layer (OPL), the hypo-reflective outer nuclear layer (ONL), and the photoreceptor layer and choroid (PR & C), which are difficult to distinguish.
Figure 6:
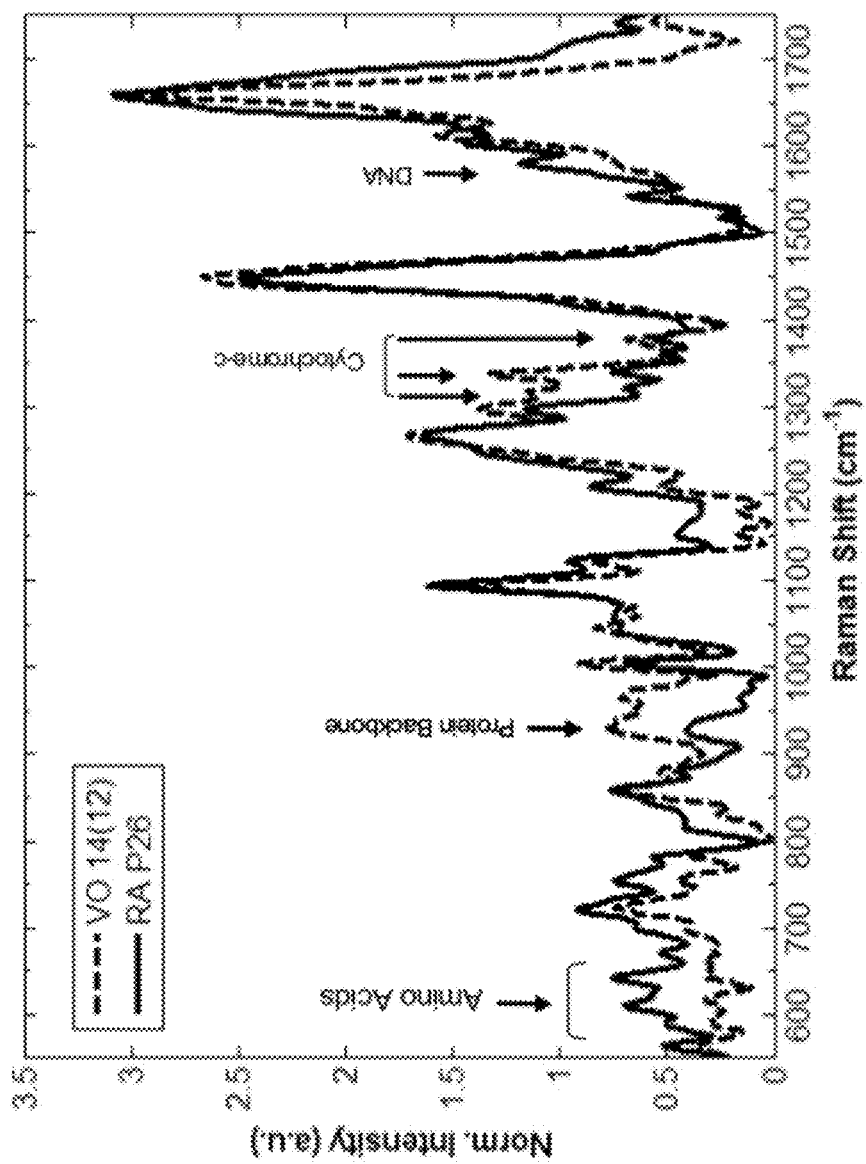
FIG. 6 shows mean VO and RA spectra after scaled subtraction of lens features. Differences are seen in peaks attributable to proteins and amino acids (610-670 $cm^{-1}$, and 929 $cm^{-1}$), DNA (1580 $cm^{-1}$), and cytochrome-c (1315-1385 $cm^{-1}$).

Referring to FIGS. 5 and 6, images and spectra are collected from a rodent model for retinopathy of prematurity (ROP), ex vivo to demonstrate the capabilities of the common detector RS-OCT system. Rat pups that have undergone a variable oxygen treatment are compared to rats raised in room air. Images and spectra collected at an age of 26 days postnatal demonstrate differences in both the thickness of the inner and outer nuclear layers, but also in the biochemical composition. In the rodent model, rats are exposed to variable-oxygen (VO) environments that alternate between hyperoxic and normoxic conditions that simulate the exposure preterm infants are subjected to after birth [40]. Here, litters of Sprague-Dawley rats are randomly separated into groups placed in either VO or room air (RA) environments. The VO rats are cycled between alternating periods of 24 hours at 50% oxygen followed by 24 hours at 10% oxygen, for 14 days. After the 14-day oxygen treatment protocol, the VO rats are moved to room air. Twelve days after removal from VO, denoted 14(12), distinct differences in the retina and retinal vasculature of the VO and age matched RA rats (denoted P26) are still persist [41]. At this point, the rats are sacrificed, and the eyes are enucleated and placed in a small vessel atop a heating pad and half-submerged with phosphate buffered saline (PBS) (pH=7.4, T=35°). The vessel is placed on a heating pad in order to maintain the temperate and mitigate the development of cold cataracts in the lens of the eye. The PBS bath and heating pad are fixed to 3-axis translation stage that allowed the sample to be appropriately positioned under the sampling optics for analysis with RS-OCT. All OCT images and Raman spectra are acquired within 30 minutes of death. All experiments are conducted in the Vanderbilt University Biomedical Optics Laboratory with protocols approved by the Institutional Animal Care and Use Committee at Vanderbilt University.

The eyes from five 14(12) rats and four P26 are evaluated to demonstrated the morphological and biochemical differences detectable with common detector RS-OCT.

FIG. 5 shows representative OCT from the 14(12) and P26 rat eyes, along with the corresponding histology sections. OCT images for analysis are generated by averaging 20 successive frames. The images demonstrate the sufficient resolution and imaging range of the system to depict the retinal structure in both the VO and RA rats. The clearest, most consistently visible layers include the hyper-reflective inner plexiform layer (IPL), a predominantly hypo-reflective band consisting of the inner nuclear layer (INL), outer plexiform layer (OPL), and outer nuclear layer (ONL), and outermost hyper-reflective regions of the eye which include the photoreceptor layers (PR) and choroid (C). Although less clear and consistent across the images, closer examination reveals the thin, hyper-reflective layer that corresponds to the nerve fiber layer at the innermost surface of the retina (NFL) proximal to a hypo-reflective band corresponding to the ganglion cell layer (GCL). Between the inner and outer nuclear layers, a thin hyper-reflective band can be made out that corresponds to the OPL.

Although the images of the VO and RA retinas appear generally similar, the thickness of the hypo-reflective band consisting primarily of the nuclear layers (NL) of the retina (INL, OPL, and ONL) is measured to determine if any physical differences could be determined by RS-OCT. The NL band is selected because it is clearly defined across all the OCT images by the bright boundaries provided by the bottom of the IPL and the top of the PR layer. In order to perform quantitative analysis, the inner and outer boundaries of the NL bands are identified through user interaction. An algorithm then a fit a polynomial to the boundaries and calculated the mean thickness, orthogonal to the surface of the outer boundary of the NL bands. The algorithm calculates the length of a vector that runs from the top of the PR layer to the bottom of the IPL, orthogonal to the surface of the PR layer, for 100 points evenly distributed across the retina. Thickness measurements are made on n=9 eyes from the VO 14(12) group and n=8 eyes from the RA P26 group. Images are not collected from one of the 14(12) eyes because temperature and corneal hydration conditions could not be maintained well enough to allow transmission of the light through to the retina. The average NL thickness of the VO 14(12) group is 119±9 µm, compared to 154±15 µm for the RA P26 group.

Following imaging, Raman spectra are acquired ($t_{acquisition}$=90 sec) from 9 positions evenly distributed across the surface of the retina for each eye. Spectra are collected from the 9 viable eyes from the 14(12) group (n=77 spectra) and the 7 viable eyes from the P26 group (n=56 spectra). Spectra are averaged across each group to create mean spectra for the VO and RA groups, which are shown in FIG. 6. The spectral features of the VO and RA retinas generally show similarities to those from the reference spectra, as well as those reported in the literature [26, 42]. The spectra show Raman peaks at 1003 cm-1 (phenylalanine), 1265 cm-1 (amide III), 1440 cm-1 (CHx), 1660 cm-1 (amide I) that are typical to most tissues because of their common occurrence in biomolecules. Examination of the differences between the VO and RA lens subtracted retina spectra show a number of bands where differences reside. Differences are seen in peaks attributable to proteins and amino acids (610-670 $cm^{-1}$, and 929 $cm^{-1}$), DNA (1580 $cm^{-1}$), and cytochrome-c (1315-1385 $cm^{-1}$). RA spectral intensity is increased at the 723, 1094, and 1580 $cm^{-1}$ peaks, which are attributed to DNA and RNA nucleotide groups [43]. Increased intensity also is seen in the band from 610 to 670 $cm^{-1}$, which has been attributed to amino acids and proteins [43]. The VO spectra exhibit differences in the peaks at 929 $cm^{-1}$, a C-C peak commonly attributed to protein backbones, and a 965 $cm^{-1}$ peak attributed to collagen molecules. In addition, the triplet of peaks in the band from 1315 to 1385 $cm^{-1}$ shows increased intensity, which has been attributed to cytochrome-c content in the retina [42].

The common detector RS-OCT system is able to both image and collect spectra from the retina. The OCT images depict the structure of the major layers of the retina typically seen in OCT images, while Raman spectra can be collected from the intact eye and processed to isolate signal primarily originating from the retina. A developmental delay is very likely to result from the VO treatment from 14(0) to 14(12), which can be measured with the RS-OCT. The Raman signatures provide information that both builds upon the morphological information seen in the OCT, as well as compliments it. The increased intensity of the DNA and amino acid peaks seems in line with the increased nuclear layer thickness measured by OCT. In humans, advanced ROP can be severe enough to result in retinal detachment with extreme irregularity in vasculature growth patterns or significant increase vascular permeability. In the animals examined here, the speed with which the pathological vasculature re-normalizes may prevent any detectable detachments with the OCT. The inability of the OCT images shown here to clearly distinguish between the photoreceptor layers, retinal pigment epithelium, and choroid likely would have made this task quite difficult in the case of minor detachments.

Spectral changes that do reflect features of in the OCT image can be particularly interesting. The spectral changes observed in the 1315 to 1385 $cm^{-1}$ range imply biochemical differences that between the VO and RA retinas that are not clearly reflected in OCT. A similar triplet of peaks is seen in work utilizing confocal RS to collect spectra from the mitochondria rich photoreceptor inner segments and attributed to cytochrome-c [42], a protein localized in the mitochondria associated with cellular metabolism. In the retina, mitochondria are localized in the photoreceptor layer, where production and turnover of the membrane bound visual pigments takes place. One possible explanation of the increased cytochrome-c content in the VO rats may be an increased level of rhodopsin generation in the developmentally delayed animals. In the case of the VO rats, a significant portion of the pathological retinal vasculature develops as tufts into the vitreous. A hypothesis for increased collagen features may be related to their necessity to maintain vitreal traction in the VO rats. The increased spectral intensity associated with C-C backbone at 929 $cm^{-1}$ is more difficult to attribute without further analysis due to its widespread presence among biomolecules. Although no clear conclusions can be drawn at this stage from any of the biochemical differences seen in the Raman spectra, it is clear that they provide unique information that can be expanded upon to better understand the molecular differences between the retinas of VO 14(12) and RA P26 animals.

The OCT resolution allows visualization of the retinal layers in the rodent model, however the overall speed and sensitivity of the instrument are sacrificed at the expense of Raman sensitivity. The maximum achievable readout rate for high-sensitivity CCD's is purposefully low in order to minimize the noise associated with higher bandwidth amplifier electronics. Similarly, CCD full well capacity is typically kept at a minimum in order to optimize dark noise performance for the benefit of the RS. Despite the fact that the detection is optimized for the Raman sensitivity, the high illumination power and long integration times necessary for the RS remain the limitations of the instrument. These parameters would surely need to be reduced for any human application; however they do not preclude feasibility in rodent models.

The results shown here demonstrate the instrument's capabilities, and provide a set of examples describing potential applications. The images and spectra from the calvaria shown in FIG. 3 demonstrate the ability of the system to characterize highly scattering tissue. In the field of bone biology, histomorphometric measurement of calvarial thickness in mouse models is a time consuming and destructive assay used to characterize bone formation. In addition to structural measures, a number of other destructive or time consuming assays are performed to characterize compositional properties related to mineralization and bone formation [29]. The clear definition of the inner and outer surfaces of the calvaria in the OCT suggests that it would be possible to perform non-destructive measurement of calvaria thickness, while compositional properties of the bone such as mineral-to-collagen ratio, mineral crystallinity, and carbonate-substitution can be calculated from analysis of the Raman spectrum [22]. The ability to perform non-destructive high resolution imaging and biochemical characterization of murine calvaria in real-time represents one example of the benefits a common-detector RS-OCT system can provide in the context of ex-vivo analysis of dissected tissues.

Biochemical and morphological analysis of retinas in animal models is another promising potential application of the common-detector RS-OCT device. Retinal imaging is the most prominent clinical application of the OCT, however recent studies have demonstrated the utility of the OCT can be extended to the evaluation of rodent models of retinal pathology as well. For example, the OCT is found to serve as a useful tool for monitoring tumor progression in a rat model of retinoblastoma [30] and retinal degeneration in a transgenic mouse model [31]. The ex vivo images of FIGS. 4($a$) and 5($a$) acquired with the common-detector RS-OCT system allow visualization of most layers of the retina, as can be confirmed by comparison to the corresponding histology cross section, as shown in FIGS. 4($b$) and 5($b$). These images certainly allow evaluation of retinal architecture, and could also be used to perform quantitative measurements of the thickness of specific retinal layers. Such analysis would be well complemented by the RS, which is capable of identifying the molecular progression of disease. For example, recent work has demonstrated the sensitivity of the RS to advanced glycation end products, which are molecules widely believed to play an important role in the ill-defined pathogenesis of age-related macular degeneration [32]. The expanding role of the OCT in animal studies coupled with the sensitivity of the RS to biochemical features invisible to OCT suggests that the common-detector RS-OCT system has the potential to become a valuable research tool for the study of retinal disease in animal models. The application of the RS-OCT system to human retinal analysis is not possible at this time, however, due to the fact that the laser exposure levels required to perform the RS are well in excess of the ANSI standards.

Figure 7:
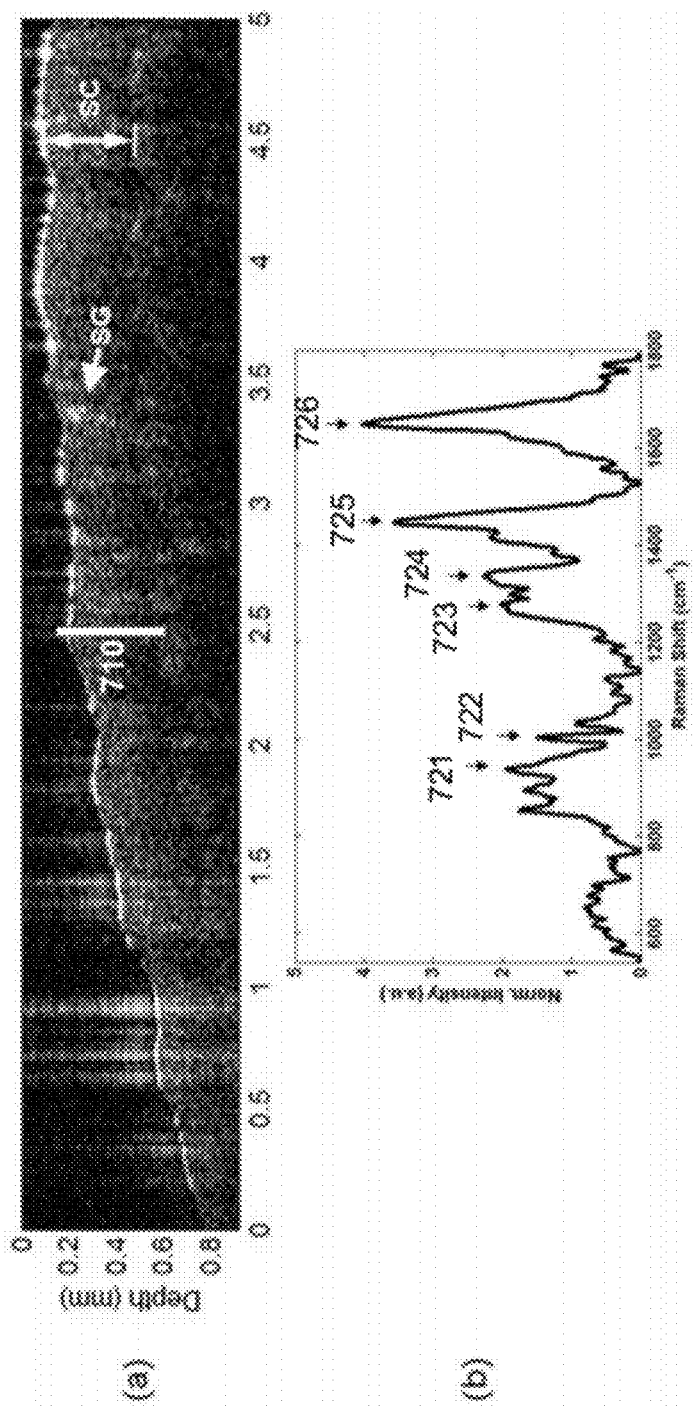
FIG. 7 shows RS-OCT evaluation of in vivo human skin on the palm of the hand, (a) OCT image, where hyper-reflective feature that is likely a Sweat Gland (SG) is seen within the stratum corneum (SC), area 710 indicates location of Raman spectrum, and axial scale assumes $n_{skin}$=1.38 [27], (b) Raman spectrum of skin, where the prominent skin peaks are identified at 936 $cm^{-1}$ (C-C backbone of collagen protein), 1003 $cm^{-1}$ (phenylalanine), 1280 $cm^{-1}$ (amide III), 1335 $cm^{-1}$ (C—H), 1440 $cm^{-1}$ ($CH_x$), and 1660 $cm^{-1}$ (amide I), which are indicated by arrows 721-726, respectively.

FIG. 7 demonstrates the ability of the integrated RS-OCT system to acquire in vivo data from human skin. The OCT image shown in FIG. 7($a$) is a single un-averaged image acquired from the palm of the hand of a volunteer. A hyper-reflective feature that is likely a Sweat Gland (SG) is seen within the stratum corneum (SC). Area 710 indicates location of Raman spectrum. Axial scale assumes $n_{skin}$=1.38 [27]. Because the image is not averaged, it depicts the minimum sensitivity of the system, which still allows visualization of distinct morphological features in the skin. The boundary between the stratum corneum and the underlying layers of the epidermis can be seen as a dark, band across the length of the image. The image also captures the presence of a hyper-reflective structure in the outer region of the epidermis that is likely a sweat gland. The position where the corresponding Raman spectrum is acquired is indicated by the red overlay. The Raman spectrum shown in FIG. 7($b$) (also a single, un-averaged acquisition, $t_{acq}$=30 sec) is representative of typical skin signatures [9], with prominent skin peaks at 936 cm$^{-1}$ (C—C backbone of collagen), 1003 cm$^{-1}$ (phenylalanine), 1280 cm$^{-1}$ (amide III), 1335 cm$^{-1}$ (C—H), 1440 cm$^{-1}$ (CH$_x$), and 1660 cm$^{-1}$ (amide I), which are indicated by arrows 721-726, respectively.

Figure 8:
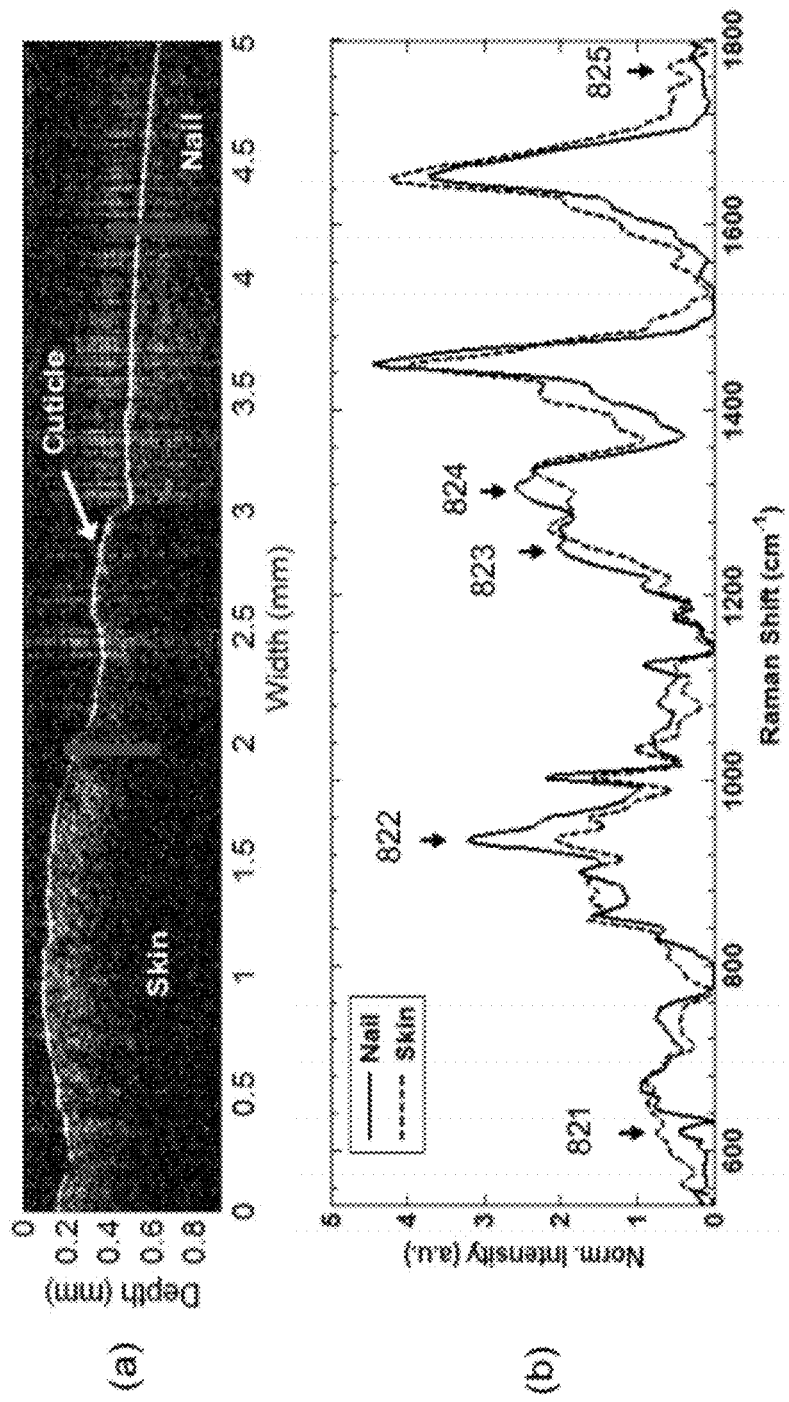
FIG. 8 shows RS-OCT evaluation of the region surrounding the proximal nail fold, (a) OCT image, where nail is labeled on the right side of the image, and inserts into the nail bed beneath the cuticle, which is located in the transverse dimension from 2.5 to 3.0 mm, to the left of the cuticle is the skin on the back of the finger, and Raman spectra acquired from the regions indicated from the red overlays, (b) Raman spectra of the skin and nail, where peaks of interest are indicated with arrows 821-825, and include the sharp 620 $cm^{-1}$ C—S peak, the 936 $cm^{-1}$ C—C protein backbone peak, the relative intensity and position of the amide III (1251 $cm^{-1}$) and C—H (1317 $cm^{-1}$) peaks, all of which are indicative of the β-sheet keratin proteins that make up the nail. In contrast, the 1770 $cm^{-1}$ lipid peak seen in soft tissue and skin is not seen in the nail.

Additionally, RS-OCT data shown in FIG. 8 is acquired from the finger of a volunteer, where the base of the fingernail inserts into the skin. Similarly, the OCT image shown in FIG. 8($a$) is un-averaged. The nail is seen on the right side of the image. The root of the nail inserts into the skin below the cuticle, which is located in the transverse dimension from 2.5 to 3.0 mm and can be seen as the raised region in the center of the image. To the left of the cuticle is the skin on the back of the finger. Raman spectra shown in FIG. 8($b$) are acquired from the nail and the skin with an acquisition time of 30 seconds for each spectrum, where peaks of interest are indicated with arrows 821-825, respectively. The location from which the spectra are acquired is indicated by the red overlays in FIG. 8($a$). The nail spectrum is characterized by features that correspond to that of keratin proteins in a β-sheet configuration. This includes the sharp, distinct nature of the 620 cm$^{-1}$ peak involved in the disulfide bonds that give keratin arrangements their strength, the relative intensity of the 936 cm$^{-1}$ C—C peak from the keratin protein backbone, the relative intensity and position of the amide III peak at 1251 cm$^{-1}$ (indicative of the β-sheet confirmation) and the C—H peak at 1317 cm$^{-1}$ [28]. All of which are indicative of the β-sheet keratin proteins that make up the nail. These features are distinct from those of the skin mentioned above. For example, the spectral difference between the skin and nail spectra at the 1770 cm$^{-1}$ lipid peak indicates of the lack of contribution from soft tissue components in the nail.

The ability of common detector RS-OCT to perform in vivo characterization of tissue morphology and biochemical composition is demonstrated through evaluation of human skin, as shown in FIG. 7. The OCT images depict the stratified nature of the skin, and can even visualize the presence of microstructural features within the stratum corneum. Based on a previously published report of the OCT in the skin that details the appearance of sweat glands in the stratum corneum [33], and the fact that the subject's skin is healthy, clean, and debris-free, which this feature is likely a sweat gland. It is unlikely the feature is simply an artifact. In spectral domain-OCT, artifacts can be seen as a result of strong reflections from the primary surface. Such artifacts can be observed near 0.9 mm in the transverse dimension of FIG. 7($a$), and are seen both above and below the primary surface. The feature the inventors believe to be a sweat gland has a much different appearance and is only seen below the skin surface. The Raman spectrum depicts signal in all the primary molecular moieties associated with the skin, including peaks associated with the collagen backbone, phenylalanine and amide I and III [34]. The ultimate strength of RS-OCT arises from it's ability to utilize OCT imaging to guide positioning of the RS probe beam, as well the instruments ability to use the RS subsystem to interrogate the biochemical composition of morphological features in an OCT image. The fundamental concept that RS-OCT is capable of characterizing both the morphological and biochemical properties of tissue is thus demonstrated through the analysis of tissues surrounding the proximal nail fold on the finger of a human volunteer.

There are a few important experimental considerations that enabled acquisition of consistent data sets from the RS-OCT system, most importantly during in vivo measurements. Namely, the speed of both the RS and OCT subsystems required the sample remain fairly stable over the course of the data acquisition times. In the case of the RS, spectral quality degraded if motion artifact is not minimized by restraining the palm or finger to a sample stage prior to measurement. Stabilization of the sample is also important in order to minimize the effect of fringe-washout, which occurs due to sample motion over the acquisition time of a single A-scan [35]. The result is noticeable image fading, which can also arise from movements and vibrations transferred to the fiber optic components of the OCT system. Thus, all the fibers are affixed to the table and instrument is built upon a vibration dampening pneumatic table. In order to minimize image distortion in OCT due to these motion-related artifacts, the spectra are collected at the fastest possible frame rate and are also unaveraged. Therefore, the images shown in FIGS. 7(a) and 8(a) represent the performance limit of the OCT subsystem with respect to sensitivity and speed. These limitations are a function of the deep-depletion, back-illuminated detector array chosen to ensure feasibility of the RS. In order to further advance potential in vivo applications of the common-detector RS-OCT system, it will certainly be necessary to incorporate an improved detector capable of improving the speed of both the RS and OCT.

Commercially available deep-depletion, back-illuminated detectors have limitations in readout rate and dynamic range, which in turn limit OCT imaging speed and sensitivity. These detectors are typically operated at slow readout rates with a premium placed on sensitivity. The corresponding detection electronics therefore have a limited bandwidth to ensure low read noise. In order to increase the imaging speed, it would be necessary to both decrease the exposure time of the detector and increase the bandwidth of the detection electronics to improve readout rates. The detected spectra in the RS are typically shot-noise limited by the relatively intense background tissue autofluorescence, which indicates that the detector speed could be increased to some degree without adversely affecting the integrity of RS. Frame transfer cameras with shorter exposure times and a second buffer array are available, and offer the potential to moderately improve the imaging performance when taking OCT "snapshots". Decreasing exposure time would reduce the susceptibility of OCT to fringe-washout, however such technology would only allow rapid acquisition of at most a few image frames and would not facilitate a faster continuous OCT frame rate. In order to further increase the OCT sensitivity based on the current system design, the sample must simply be illuminated with increased laser power without saturating the detector. Currently, the detector is illuminated very near the saturation level, which is typically proportional to the full well capacity of the detector elements. A detector with increased pixel full well capacity and thus increased saturation levels would alleviate this constraint. However, such a detector is not currently available from standard commercial manufacturers. Nevertheless, the realization of a detector with the properties described above could improve the OCT imaging performance and improve the in vivo imaging potential of the device.

In addition to improving the sensitivity of OCT imaging, increasing the achievable imaging depth would also benefit the system's ease of use and imaging performance. As previously described, the OCT spectral resolution limits the achievable imaging depth range to about 1.27 mm. Although this imaging range exceeds the optical penetration depth of the 855 nm source in the samples that is imaged above, an expanded range would simplify localization of the sample as well as mitigate the depth dependent sensitivity roll-off that results from the finite spectrograph spectral resolution [36]. The OCT spectral resolution in the system is limited by the horizontal size of the individual CCD pixels. Decreasing the horizontal pixel size and increasing the number of horizontal pixels from 1024 to 2048 would be beneficial. In addition, as seen in FIG. 2(c), the detectable spectral range begins at about 780 nm, despite the fact that the OCT source intensity falls below the noise floor near 800 nm and the RS filter cutoff occurs at about 818 nm. If a CCD with increased pixel density is obtained, limiting illumination of the CCD to the 800-920 nm spectral band with a custom grating would further improve the spectral resolution, thereby expanding the achievable imaging range, and increasing imaging performance as a function of depth.

Despite the fact that the camera used in the above examples can benefit from further optimization, the ability of a commercially available detector commonly used in tissue RS to acquire OCT images of microstructural details in tissue is demonstrated. The significance of this demonstration lies in the implication that a few important modifications to an existing RS instrument can enable OCT imaging at a fraction of the cost of adapting an existing OCT instrument to perform the RS. The essential components to perform this modification include the OCT light source, a 2×2 fiber coupler, and an input adapter for the spectrograph, along with the appropriate optics for the reference and sample arms. Two-dimensional OCT images can be generated by translating the sample with a motorized stage in place scanning the sampling beam with a galvanometer. The system can be further simplified by replacing the components that automate the transition between the OCT and RS (MEMS optical switch and the translation stage mounted mirror in the sample arm) with manual flip mirrors. Although these simplifications would come at the expense of the system's ease of use, they provide basic design guidelines that would enable current users of the RS to complement biochemically specific spectra with OCT images of tissue microstructures. Another common wavelength source for tissue RS is about 830 nm. However, as previously stated, there are no OCT sources that overlap the 830 nm RS "fingerprint" region known to the inventors. If an OCT source with a spectral range that is fully detected within the range covered by typical 830 nm RS spectrographs (830-1000 nm), it would certainly be well suited for incorporation into the RS-OCT system similar to that described here. Alternatively, adaptation of the spectrograph dispersion to cover the appropriate spectral ranges of an existing OCT source and the 830 nm RS "fingerprint" region is also possible, granted a sufficient spectral resolution is achieved.

The invented RS-OCT system represents a development of the dual-modal RS-OCT systems [13, 14]. However, alternative approaches have been reported to combine the biochemical specificity of vibrational spectroscopy with high resolution morphological imaging. Techniques utilizing coherent anti-stokes Raman spectroscopy (CARS) have been reported for in vivo video-rate microscopy [37], as well as CARS based interferometric imaging [38]. However, the cost of the ultrafast laser sources necessary for such approaches contrasts starkly with the simplicity of the stripped down common-detector RS-OCT system proposed in the previous paragraph.

The benefit of complementing Raman spectral analysis with OCT imaging is based on the fact that point-wise RS provides no direct spatially relevant information. Accordingly, OCT images can be useful to guide positioning of the Raman probe beam as well as provide contextual morphological and microstructural information to benefit tissue characterization. Similarly, Raman spectra can provide information related to the biochemical content of features within an OCT image, as well as valuable data related to general compositional properties that are not directly accessible from images of tissue reflectivity. The underlying value of the RS-OCT system is based on the complementary nature of the RS and OCT data sets, and could be applicable to a wide range of applications beyond those demonstrated here. Biochemical and morphological analysis can potentially assist in screening and diagnosis of diseases such as cancer, enhance the guidance and monitoring of medical therapies, and even benefit non-biomedical applications where high-resolution cross sectional imaging and high specificity compositional analysis are critical, such as art preservation and restoration.

In brief, the present invention, among other things, recites a combined RS-OCT system with a single detection arm that is capable of acquiring both morphological and biochemical features of tissues. While previous implementations of the RS-OCT simply provided co-aligned sampling beams, the invented RS-OCT system uses a common detection arm to perform both the RS and OCT. The significance of the common detector design lies in the fact that it reduces the hardware requirements for RS-OCT and simplifies implementation. The system uses a single spectrograph to perform 855 nm OCT in the spectral domain, and RS with a 785 nm source whose biological fingerprint spectral range overlaps the OCT bandwidth. The two beams are co-aligned in the sample arm, allowing the system to perform sequential, co-registered acquisition of the complementary data sets. The OCT can be performed at 2 frames/sec with a sensitivity of about −86 dB and a spatial resolution of about 8 μm (axial, in tissue) by about 18 μm (transverse). Averaging consecutive frames allows the imaging sensitivity to improved to better than about −100 dB. Tissue Raman spectra corresponding to specific A-scans in the OCT image are acquired in about 30 sec with about 40 mW of laser power. The capabilities of the instrument are demonstrated ex vivo in the calvaria and retina of rodents, and in vivo in human skin.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments are chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

List of References

[1]. J. G. Fujimoto, M. E. Brezinski, G. J. Tearney, S. A. Boppart, B. Bouma, M. R. Hee, J. F. Southern and E. A. Swanson, "Optical biopsy and imaging using optical coherence tomography," Nat Med 1(9), 970-972 (1995).

[2]. A. Mahadevan-Jansen, "Raman Spectroscopy: From Benchtop to Bedside," in Biomedical Photonics Handbook T. Vo Dinh, Ed., pp. 30:31-27, CRC Press, Boca Raton, Fla. (2003).

[3]. C. Bowd, L. M. Zangwill, C. C. Berry, E. Z. Blumenthal, C. Vasile, C. Sanchez-Galeana, C. F. Bosworth and P. A. Sample, "Detecting early glaucoma by assessment of retinal nerve fiber layer thickness and visual function," Invest Ophth Vis Sci 42(9), 1993-2003 (2001).

[4]. G. Zuccaro, N. Gladkova, J. Vargo, F. Feldchtein, E. Zagaynova, D. Conwell, G. Falk, J. Goldblum, J. Dumot, J. Ponsky, G. Gelikonov, B. Davros, E. Donchenko and J. Richter, "Optical coherence tomography of the esophagus and proximal stomach in health and disease," Am J Gastroenterol 96(9), 2633-2639 (2001).

[5]. M. Mogensen, T. M. Joergensen, B. M. Nurnberg, H. A. Morsy, J. B. Thomsen, L. Thrane and G. B. Jemec, "Assessment of optical coherence tomography imaging in the diagnosis of non-melanoma skin cancer and benign lesions versus normal skin: observer-blinded evaluation by dermatologists and pathologists," Dermatol Surg 35(6), 965-972 (2009).

[6]. F. J. van der Meer, D. J. Faber, D. M. B. Sassoon, M. C. Aalders, G. Pasterkamp and T. G. van Leeuwen, "Localized measurement of optical attenuation coefficients of atherosclerotic plaque constituents by quantitative optical coherence tomography," Ieee T Med Imaging 24(10), 1369-1376 (2005).

[7]. I. Cilesiz, P. Fockens, R. Kerindongo, D. Faber, G. Tytgat, F. ten Kate and T. van Leeuwen, "Comparative optical coherence tomography imaging of human esophagus: How accurate is localization of the muscularis mucosae?," Gastrointest Endosc 56(6), 852-857 (2002).

[8]. A. Mahadevan-Jansen, M. F. Mitchell, N. Ramanujam, A. Malpica, S. Thomsen, U. Utzinger and R. Richards-Kortum, "Near-infrared Raman spectroscopy for in vitro detection of cervical precancers," Photochem Photobiol 68(1), 123-132 (1998).

[9]. C. A. Lieber, S. K. Majumder, D. L. Ellis, D. D. Billheimer and A. Mahadevan-Jansen, "In vivo nonmelanoma skin cancer diagnosis using Raman microspectroscopy," Laser Surg Med 40(7), 461-467 (2008).

[10]. A. S. Haka, K. E. Shafer-Peltier, M. Fitzmaurice, J. Crowe, R. R. Dasari and M. S. Feld, "Diagnosing breast cancer by using Raman spectroscopy," Proc Natl Acad Sci USA 102(35), 12371-12376 (2005).

[11]. M. G. Shim, L. M. Song, N. E. Marcon and B. C. Wilson, "In vivo near-infrared Raman spectroscopy: demonstration of feasibility during clinical gastrointestinal endoscopy," Photochem Photobiol 72(1), 146-150 (2000).

[12]. A. C. Ko, L. P. Choo-Smith, M. Hewko, L. Leonardi, M. G. Sowa, C. C. Dong, P. Williams and B. Cleghorn, "Ex vivo detection and characterization of early dental caries by optical coherence tomography and Raman spectroscopy," J Biomed Opt 10(3), 031118 (2005).

[13]. C. A. Patil, N. Bosschaart, M. D. Keller, T. G. van Leeuwen and A. Mahadevan-Jansen, "Combined Raman spectroscopy and optical coherence tomography device for tissue characterization," Opt Lett 33(10), 1135-1137 (2008).

[14]. J. W. Evans, R. J. Zawadzki, R. Liu, J. W. Chan, S. M. Lane and J. S. Werner, "Optical coherence tomography and Raman spectroscopy of the ex-vivo retina," J Biophotonics 2(6-7), 398-406 (2009).

[15]. J. J. Baraga, M. S. Feld and R. P. Rava, "Rapid near-Infrared Raman-Spectroscopy of Human Tissue with a Spectrograph and Ccd Detector," Appl Spectrosc 46(2), 187-190 (1992).

[16]. G. Hausler and M. W. Lindner, ""Coherence Radar" and "Spectral Radar"—New Tools for Dermatological Diagnosis," J Biomed Opt 3(1), 21-31 (1998).

[17]. N. N. Boustany, R. Manoharan, R. R. Dasari and M. S. Feld, "Ultraviolet resonance Raman spectroscopy of bulk and microscopic human colon tissue," Appl Spectrosc 54(1), 24-30 (2000).

[18]. T. Kawabata, T. Mizuno, S. Okazaki, M. Hiramatsu, T. Setoguchil, H. Kikuchi, M. Yamamoto, Y. Hiramatsu, K. Kondo, M. Baba, M. Ohta, K. Kamiya, T. Tanaka, S. Suzuki and H. Konno, "Optical diagnosis of gastric cancer using near-infrared multichannel Raman spectroscopy with a 1064-nm excitation wavelength," J Gastroenterol 43(4), 283-290 (2008).

[19]. R. Leitgeb, C. K. Hitzenberger and A. F. Fercher, "Performance of fourier domain vs. time domain optical coherence tomography," Opt Express 11(8), 889-894 (2003).

[20]. M. Wojtkowski, R. Leitgeb, A. Kowalczyk, T. Bajraszewski and A. F. Fercher, "In vivo human retinal imaging by Fourier domain optical coherence tomography," J Biomed Opt 7(3), 457-463 (2002).

[21]. C. A. Lieber and A. Mahadevan-Jansen, "Automated method for subtraction of fluorescence from biological Raman spectra," Appl Spectrosc 57(11), 1363-1367 (2003).

[22]. A. Carden and M. D. Morris, "Application of vibrational spectroscopy to the study of mineralized tissues (review)," J Biomed Opt 5(3), 259-268 (2000)

[23]. A. Ascenzi and C. Fabry, "Technique for dissection and measurement of refractive index of osteones," J Biophys Biochem Cytol 6(1), 139-142 (1959).

[24]. J. A. Izatt, A. M. Rollins, R. Ung-arunyawee, S. Yazdanfar and M. D. Kulkami, "System Integration and Signal/Image Processing," in Handbook of Optical Coherence Tomography B. Bouma and G. Tearney, Eds., pp. 143-174, Marcel Dekker, New York (2002).

[25]. J. R. Beattie, S. Brockbank, J. J. McGarvey and W. J. Curry, "Effect of excitation wavelength on the Raman spectroscopy of the porcine photoreceptor layer from the area centralis," Mol Vis 11(825-832 (2005).

[26]. J. R. Beattie, S. Brockbank, J. J. McGarvey and W. J. Curry, "Raman microscopy of porcine inner retinal layers from the area centralis," Mol Vis 13(1106-1113 (2007).

[27]. H. F. Ding, J. Q. Lu, W. A. Wooden, P. J. Kragel and X. H. Hu, "Refractive indices of human skin tissues at eight wavelengths and estimated dispersion relations between 300 and 1600 nm," Phys Med Biol 51(6), 1479-1489 (2006).

[28]. H. G. M. Edwards, D. E. Hunt and M. G. Sibley, "FT-Raman spectroscopic study of keratotic materials: horn, hoof and tortoiseshell," Spectrochimica Acta Part A: Molecular and Biomolecular Spectroscopy 54(5), 745-757 (1998).

[29]. T. R. Arnett and B. Henderson, Methods in Bone Biology, Chapman and Hall, New York (1998).

[30]. M. Ruggeri, G. Tsechpenakis, S. Jiao, M. E. Jockovich, C. Cebulla, E. Hernandez, T. G. Murray and C. A. Puliafito, "Retinal tumor imaging and volume quantification in mouse model using spectral-domain optical coherence tomography," Opt Express 17(5), 4074-4083 (2009).

[31]. K. H. Kim, M. Puoris'haag, G. N. Maguluri, Y. Umino, K. Cusato, R. B. Barlow and J. F. de Boer, "Monitoring mouse retinal degeneration with high-resolution spectral-domain optical coherence tomography," J Vis 8(1), 17 11-11 (2008).

[32]. J. V. Glenn, J. R. Beattie, L. Barrett, N. Frizzell, S. R. Thorpe, M. E. Boulton, J. J. McGarvey and A. W. Stitt, "Confocal Raman microscopy can quantify advanced glycation end product (AGE) modifications in Bruch's membrane leading to accurate, nondestructive prediction of ocular aging," Faseb J 21(13), 3542-3552 (2007).

[33]. J. Lademann, N. Otberg, H. Richter, L. Meyer, H. Audring, A. Teichmann, A. Kniittel and W. Sterry, "Application of optical non-invasive methods in skin physiology: a comparison of laser scanning microscopy and optical coherent tomography with histological analysis," Skin Research and Technology 13(2), 119-132 (2007).

[34]. P. J. Caspers, G. W. Lucassen, R. Wolthuis, H. A. Bruining and G. J. Puppels, "In vitro and in vivo Raman spectroscopy of human skin," Biospectroscopy 4(5 Suppl), S31-39 (1998).

[35]. S. H. Yun, G. Tearney, J. de Boer and B. Bouma, "Motion artifacts in optical coherence tomography with frequency-domain ranging," Opt Express 12(13), 2977-2998 (2004).

[36]. C. Dorrer, N. Belabas, J. P. Likforman and M. Joffre, "Spectral resolution and sampling issues in Fourier-transform spectral interferometry," J. Opt. Soc. Am. B-Opt. Phys. 17(10), 1795-1802 (2000).

[37]. C. L. Evans, E. O. Potma, M. Puoris'haag, D. Cote, C. P. Lin and X. S. Xie, "Chemical imaging of tissue in vivo with video-rate coherent anti-Stokes Raman scattering microscopy," P Natl Acad Sci USA 102(46), 16807-16812 (2005)

[38]. D. L. Marks and S. A. Boppart, "Nonlinear interferometric vibrational imaging," Phys Rev Lett 92(12), -(2004).

[39]. Leitgeb, R., Hitzenberger, C. K. and Fercher, A. F., "Performance of fourier domain vs. time domain optical coherence tomography," Optics Express 11(8), 889-894 (2003).

[40]. Penn, J. S., Tolman, B. L. and Lowery, L. A., "Variable oxygen exposure causes preretinal neovascularization in the newborn rat," Invest Ophthalmol Vis Sci 34(3), 576-585 (1993).

[41]. Roberto, K. A., Tolman, B. L. and Penn, J. S., "Long-term retinal vascular abnormalities in an animal model of retinopathy of prematurity," Curr Eye Res 15(9), 932-937 (1996).

[42]. Beattie, J. R., Brockbank, S., McGarvey, J. J. and Curry, W. J., "Effect of excitation wavelength on the Raman spectroscopy of the porcine photoreceptor layer from the area centralis," Mol Vis 11(825-832 (2005).

[43]. Mahadevan-Jansen, A. and Richards-Kortum, R., "Raman Spectrscopy for the Detection of Cancers and Precancers," Journal of Biomedical Optics 1(1), 31-70 (1996).

What is claimed is:

1. An apparatus of combining Raman spectroscopy (RS) and optical coherence tomography (OCT) for non-invasively evaluating a target of interest of a living subject, comprising:
   (a) a first light source for generating a broadband light characterized with a center wavelength and a spectral bandwidth;
   (b) a second light source for generating a monochromatic light at a single wavelength, wherein the first and second light sources are adapted such that resultant Raman scattering spectrum and OCT bandwidth have a spectral overlap with each other;
   (c) a beamsplitter optically coupled to the first light source for receiving the broadband light and splitting the received broadband light into a reference light and a sample light;
   (d) a reference arm optically coupled to the beamsplitter for receiving the reference light and returning the received reference light into the beamsplitter;
   (e) a sample arm optically coupled to the beamsplitter and the second light source for combining the sample light and the monochromatic light, delivering the combined sample and monochromatic light to the target of interest, collecting a backscattering light and a Raman scattering light that are generated from interaction of the sample light and the monochromatic light with the target of interest, respectively, returning the backscattering light into the beamsplitter so as to generate an interference signal between the returned backscattering light and the returned reference light in the beamsplitter, and directing the Raman scattering light in an output optical path; and (f) a single detector optically coupled to the beamsplitter for collecting the interference signal to provide an interference pattern of the returned backscattering light and the returned reference light, and to the sample arm for collecting the Raman scattering light from the output optical path to provide the Raman scattering spectrum, respectively.

2. The apparatus of claim 1, wherein the sample arm comprises:

(a) a collimating lens (CL) optically coupled to the beamsplitter for receiving the sample light and collimating the received sample light into a first optical path;

(b) a mirror (M) positioned for reflecting the collimated sample light from the first optical path to a second optical path;

(c) a translatable mirror (TM) placed at the second optical path for transmitting the reflected sample light along the second optical path;

(d) a dichroic mirror (DM) placed at the second optical path for transmitting the sample light received from the translatable mirror (TM) along the second optical path and reflecting the monochromatic light received from a third optical path into the second optical path, respectively, such that the transmitted sample light and the reflected monochromatic light are combined in the second optical path;

(e) a scanning member placed at the second optical path for directing the combined sample and monochromatic light received from the dichroic mirror (DM) to a target of interest along a fourth optical path; and (f) an objective lens (OL) placed at the fourth optical path for focusing the directed sample and monochromatic light received from the scanning member onto the target of interest, wherein in response, the target of interest backscatters the sample light and the monochromatic light in the forms of a backscattering light and a Raman scattering light, respectively, which are collected and focused to the scanning member by the objective lens (OL), directed by the scanning member along the second optical path to the dichroic mirror (DM), and transmitted by the dichroic mirror (DM) along the second optical path to the translatable mirror (TM), from which the Raman scattering light is reflected to a long pass (LP) filter along the output optical path, while the backscattering light is transmitted along the second optical path to the mirror (M) and reflected thereby along the first optical path to the collimating lens (CL).

3. The apparatus of claim 2, wherein the sample arm further comprises a dual-band pass filter (BP) and a spatial filter (SF) placed at the third optical path between the dichroic mirror (DM) and the second light source.

4. The apparatus of claim 3, wherein the dual-band pass filter (BP) is characterized with a central bandpass wavelength corresponding to a wavelength of the monochromatic light.

5. The apparatus of claim 2, wherein the sample arm further comprises a coupling lens (C) placed at the output optical path for coupling the Raman scattering light transmitted from the long pass (LP) filter to a multimode fiber that is optically connected to the detector.

6. The apparatus of claim 2, wherein the scanning member comprises at least one of micro-electronic mirrors (MEMS), micro-optoelectrical mirrors (MOEMS), galvanometer devices, rotation motors, and translational motors.

7. The apparatus of claim 2, further comprising an MEMS optical switch (MOS) optically coupled between the beamsplitter and the detector.

8. The apparatus of claim 7, wherein the MEMS optical switch (MOS), the translatable mirror (TM) and the scanning member are configured such that during an OCT mode, the scanning member scans the combined sample and monochromatic light across the target of interest, the MEMS optical switch (MOS) directs the interference signal received from the beamsplitter to the detector, while the translatable mirror (TM) is positioned such that the Raman scattering light is not collected.

9. The apparatus of claim 8, wherein during a Raman mode, the scanning member is fixed, the MEMS optical switch (MOS) directs the light received from the beamsplitter away from the detector, while the translatable mirror (TM) reflects the Raman scattering light into the fifth optical path that is coupled to the detector.

10. The apparatus of claim 9, further comprising a multifunction DAQ device for controlling the MEMS optical switch (MOS), the translatable mirror (TM), and the scanning member.

11. The apparatus of claim 1, wherein the reference arm is arranged such that the length of an optical path of the reference light propagating from the beamsplitter through the reference arm and back to the beamsplitter is adjustable.

12. The apparatus of claim 11, wherein the sample light transmits from the beamsplitter through the sample arm to the target of interest, and is backscattered by the target of interest into the beamsplitter through the sample arm along a sample path having a length that is adjustable depending upon the structure of the target of interest to be examined.

13. The apparatus of claim 12, further comprising three polarization control (PC) paddles optically coupled between the first light source and the beamsplitter, between the beamsplitter and the reference arm, and between the beamsplitter and the sample arm, respectively.

14. The apparatus of claim 1, wherein the first light source comprises light emitting diodes (LEDs), femtosecond lasers or broadband optical amplifiers, and wherein the second light source comprises a laser.

15. The apparatus of claim 14, wherein the broadband light is characterized with a center wavelength is about 855 nm, and a spectral bandwidth is about 40 nm, and wherein the monochromatic light has a single wavelength is 785 nm.

16. The apparatus of claim 15, wherein the detector comprises back-illuminated, deep-depletion CCD arrays with cooling mechanisms and a spectrograph that is configured to cover a wavelength range of about 780-920 nm.

17. The apparatus of claim 1, wherein the beamsplitter comprises an OCT 2×2 fiber coupler.

18. The apparatus of claim 1, wherein the interference pattern contains information of morphological details of the target of interest, and wherein the frequency spectrum contains information of biochemical contents of the target of interest.

19. The apparatus of claim 18, wherein the interference pattern of the interference signal is associated with an optical coherence tomographic (OCT) image, and wherein a spectral profile of the Raman scattering spectrum includes a plurality of intensity peaks at a plurality of wavelengths, each intensity peak associating with a specific biochemical content of the target of interest.

20. The apparatus of claim 19, further comprising a controller in communication with the detector and programmed to correlate the OCT image with the Raman scattering spectrum and determine the structures and biochemical content of the target of interest from the correlated OCT image and Raman scattering spectrum.

21. The apparatus of claim 20, wherein the controller is a computer having a display for displaying the OCT image and the Raman scattering spectrum.

22. An apparatus for non-invasively evaluating a target of interest of a living subject, comprising:
  (a) an optical coherence tomography (OCT) system, comprising;
    a broadband light source for emitting a broadband light;
    a beamsplitter for splitting the broadband light into a reference light and a sample light;
    a reference arm optically coupled to the beamsplitter for receiving the reference light and returning the received reference light into the beamsplitter; and
    a sample arm optically coupled to the beamsplitter for receiving the sample light and delivering the received sample light to the target of interest, collecting a backscattering light generated from interaction of the sample light with the target of interest, returning the backscattering light into the beamsplitter so as to generate an interference signal between the returned backscattering light and the returned reference light in the beamsplitter;
  (b) a Raman spectroscopy (RS) system, comprising a monochromatic light source optically coupled to the sample arm for emitting a monochromatic light, wherein the monochromatic light is co-aligned with the sample light and delivered to the target of interest by the sample arm, wherein a Raman scattering light is generated from the target of interest interacting with the monochromatic light, and wherein the Raman scattering light is collected and directed by the sample arm to an output optical path; and
  (c) a single detector optically coupled to the beamsplitter for collecting the interference signal to provide an interference pattern of the returned backscattering light and the returned reference light, and to the sample arm for collecting the Raman scattering light from the output optical path to provide a Raman scattering spectrum, respectively.

23. The apparatus of claim 22, wherein an OCT image and the Raman scattering spectrum are sequentially acquired.

24. The apparatus of claim 22, wherein the reference arm is arranged such that the length of an optical path of the reference light propagating from the beamsplitter through the reference arm and back to the beamsplitter is adjustable.

25. The apparatus of claim 24, wherein the sample light transmits from the beamsplitter through the sample arm to the target of interest, and is backscattered by the target of interest into the beamsplitter through the sample arm along a sample path having a length that is adjustable depending upon the structure of the target of interest to be examined.

26. The apparatus of claim 22, wherein the broadband and monochromatic light sources are adapted such that resultant Raman scattering spectra and OCT bandwidth have a spectral overlap with each other.

27. The apparatus of claim 26, wherein the broadband light is characterized with a center wavelength about 855 nm, and a spectral bandwidth about 40 nm, and wherein the monochromatic light has a single wavelength about 785 nm.

28. The apparatus of claim 27, wherein the detector comprises back-illuminated, deep-depletion CCD arrays with cooling mechanisms and a spectrograph that is configured to cover a wavelength range of about 780-920 nm.

29. The apparatus of claim 22, wherein the interference pattern contains information of morphological details of the target of interest, and wherein the Raman scattering spectrum contains information of biochemical contents of the target of interest.

30. The apparatus of claim 29, wherein the interference pattern of the interference signal is associated with an optical coherence tomographic (OCT) image, and wherein a spectral profile of the Raman scattering spectrum includes a plurality of intensity peaks at a plurality of wavelengths, each intensity peak associating with a specific biochemical content of the target of interest.

* * * * *